United States Patent
Strom et al.

(10) Patent No.: US 9,327,866 B2
(45) Date of Patent: May 3, 2016

(54) CARTON HOLDER WITH DISPENSING CONFIGURATIONS, SYSTEM, AND METHOD OF USE

(71) Applicant: Welch Allyn, Inc., Skaneateles Falls, NY (US)

(72) Inventors: John R. Strom, Skaneateles Falls, NY (US); Michael T. McMahon, Skaneateles Falls, NY (US); Sean R. Karla, Skaneateles Falls, NY (US); Lisa Killian, Skaneateles Falls, NY (US)

(73) Assignee: WELCH ALLYN, INC., Skaneateles Falls, NY (US)

( * ) Notice: Subject to any disclaimer, the term of this patent is extended or adjusted under 35 U.S.C. 154(b) by 404 days.

(21) Appl. No.: 13/754,526

(22) Filed: Jan. 30, 2013

(65) Prior Publication Data
US 2014/0209504 A1    Jul. 31, 2014

(51) Int. Cl.
*B65D 5/54* (2006.01)
*B65D 5/63* (2006.01)
*B65D 83/08* (2006.01)
*A61B 5/022* (2006.01)

(52) U.S. Cl.
CPC ............... *B65D 5/542* (2013.01); *B65D 83/08* (2013.01); *A61B 5/02233* (2013.01)

(58) Field of Classification Search
USPC .......... 229/243, 242, 240, 244; 206/499, 774; 220/266, 270, 279
See application file for complete search history.

(56) References Cited

U.S. PATENT DOCUMENTS

| | | | |
|---|---|---|---|
| D242,510 S | 11/1976 | Enckler | |
| 4,946,042 A * | 8/1990 | Ferreri et al. | 229/241 |
| 5,251,819 A | 10/1993 | McHugh | |
| 5,505,372 A | 4/1996 | Edson et al. | |
| 5,622,309 A * | 4/1997 | Matsuda et al. | 229/243 |
| D419,440 S | 1/2000 | Hansen | |
| D421,531 S | 3/2000 | Haas | |
| D431,462 S | 10/2000 | Menaged et al. | |
| D432,912 S | 10/2000 | Lubineau-Bigot et al. | |

(Continued)

FOREIGN PATENT DOCUMENTS

JP    2003-095260 A    4/2003

OTHER PUBLICATIONS

Application for Registration of an Industrial Design Examiner's Report for Application No. 152251; dated Mar. 12, 2014.

(Continued)

*Primary Examiner* — Mickey Yu
*Assistant Examiner* — Allan Stevens

(57) ABSTRACT

Systems and apparatuses directed to cartons with user selectable dispensing configurations. An example carton for dispensing a plurality of products stored therein includes a first removable feature configured to be selectively removed from a top surface to enable removal of a portion of a first end; a second removable feature configured to be selectively removed from the top surface to enable removal of a portion of a second end; and a third removable feature configured to be selectively removed from the top surface to enable removal of a portion of the top surface. The carton defines a closed configuration and a dispensing configuration that is defined by at least one of the portion of the first end being removed, the portion of the second end being removed, or the portion of the top surface being removed. Methods for manufacturing a carton with user selectable dispensing configurations are also contemplated.

13 Claims, 23 Drawing Sheets

(56) References Cited

U.S. PATENT DOCUMENTS

| | | |
|---|---|---|
| D433,630 S | 11/2000 | Lubineau-Bigot et al. |
| D472,463 S | 4/2003 | Kinigakis |
| D473,378 S | 4/2003 | Bellersheim |
| D490,703 S | 6/2004 | Rusnock |
| D505,620 S | 5/2005 | Huebsch |
| D511,681 S | 11/2005 | Cogley et al. |
| D548,583 S | 8/2007 | Carmichael et al. |
| D551,007 S | 9/2007 | Trinko |
| D554,419 S | 11/2007 | Thompson et al. |
| 7,328,798 B2 * | 2/2008 | Auclair et al. .......... 206/427 |
| D570,201 S | 6/2008 | Decker et al. |
| D583,872 S | 12/2008 | Smith |
| 7,743,944 B2 | 6/2010 | Ho Fung et al. |
| 7,784,675 B2 | 8/2010 | Sutherland et al. |
| D628,387 S | 12/2010 | Klein et al. |
| 8,033,449 B2 * | 10/2011 | Ho Fung et al. ......... 229/122.1 |
| D650,175 S | 12/2011 | Lee |
| 8,136,717 B2 | 3/2012 | De Paula et al. |
| D670,913 S | 11/2012 | Lee |
| D674,637 S | 1/2013 | London |
| D678,049 S | 3/2013 | Bakker et al. |
| D699,101 S | 2/2014 | Strom et al. |
| 2003/0164317 A1 * | 9/2003 | Fujiwara .................. 206/425 |
| 2006/0255105 A1 | 11/2006 | Sweet |
| 2007/0090175 A1 * | 4/2007 | Schemmel ............... 229/242 |
| 2007/0267466 A1 | 11/2007 | Brand et al. |
| 2010/0140337 A1 * | 6/2010 | Brand ...................... 229/243 |
| 2010/0298724 A1 | 11/2010 | Vivenzio et al. |

OTHER PUBLICATIONS

Application for Registration of an Industrial Design Examiner's Report for Application No. 152254; dated Mar. 12, 2014.
Application for Registration of an Industrial Design Examiner's Report for Application No. 152255; dated Mar. 12, 2014.
International Search Report for International Application No. PCT/US2013/074545 mailed Mar. 26, 2014 (3 pgs.).
International Preliminary Report on Patentability for International Application No. PCT/US2013/074545 mailed Aug. 13, 2015 (12 pgs.).

* cited by examiner

CARTON HOLDER WITH DISPENSING CONFIGURATIONS, SYSTEM, AND METHOD OF USE

FIELD OF THE INVENTION

Embodiments of the present invention relate generally to cartons for shipping and dispensing a plurality of products, and more particularly, relate to cartons with user selectable dispensing configurations.

BACKGROUND OF THE INVENTION

Often times multiples of the same product need to be packaged together and shipped to a customer. In some cases, depending on the type of product being shipped, it may also be beneficial to provide for dispensing of one or more of the products, such as to an end user. This is often the case with frequently used products, such as disposable products.

Thus, there is a need to maintain reduced shipment and packaging costs while still providing an effective means for dispensing the product.

BRIEF SUMMARY OF THE INVENTION

In order to address the above noted needs, some embodiments of the present invention provide a carton that is configured to store a plurality of products for shipping while also providing dispensing configurations for dispensing the plurality of products from the carton. In such a regard, in some embodiments, the carton may comprise material that can be torn or at least partially removed to form a dispensing configuration.

Additionally, in some cases, the positioning of the carton may vary depending on the customer and available space. Indeed, the customer may wish to position the carton on a desk, mount the carton to a wall, fit the carton in a narrow space, etc. As such, some embodiments of the present invention provide a carton with a plurality of removable features that enable different dispensing configurations. Indeed, depending on the positioning of the carton for dispensing, the customer may wish to create a certain dispensing configuration. In light of the foregoing background, some embodiments of the present invention provide cartons configured to store a plurality of products and provide for user selectable dispensing configurations.

In some cases, a particular product may be targeted for shipment and dispensing within some example cartons described herein. Moreover, such a product may have additional requirements or preferences during dispensing that can be addressed by some example dispensing configurations described herein. For example, some embodiments of the present invention contemplate use with disposable blood pressure cuffs. Indeed, as the number of blood pressure cuffs used within an examination area increases, a need has been created to provide a carton with a dispensing configuration that promotes dispensing of disposable blood pressure cuffs in an efficient manner. Along these same lines, blood pressure cuffs commonly have a number of irregular surfaces (e.g., ports, tubes, and attachment surfaces) that may engage adjacent cuffs. Moreover, it is beneficial to prevent cross-contamination between adjacent disposable blood pressure cuffs. As such, in some embodiments, the carton may define one or more dispensing configurations that orient the cuffs in a certain manner and promote dispensing of only one cuff at a time.

In one example embodiment, a carton for dispensing a plurality of products stored therein is provided. The carton defines a top surface, a bottom surface, a first end, and a second end. The carton comprises a first removable feature associated with the top surface and positioned proximate the first end. The first removable feature is configured to be selectively removed from the top surface to enable removal of a portion of the first end. The carton further comprises a second removable feature associated with the top surface and positioned proximate the second end. The second removable feature is configured to be selectively removed from the top surface to enable removal of a portion of the second end. The carton further comprises a third removable feature associated with the top surface and positioned between the first removable feature and the second removable feature. The third removable feature is configured to be selectively removed from the top surface to enable removal of a portion of the top surface. The carton defines a closed configuration and a dispensing configuration. The dispensing configuration is defined by at least one of the portion of the first end being removed, the portion of the second end being removed, or the portion of the top surface being removed.

In some embodiments, the dispensing configuration is defined by the portion of the first end being removed to reveal a first portion of each product for dispensing. Additionally, in some embodiments, the dispensing configuration is further defined by the first portion of each product being supported by the bottom surface and a back surface of the carton. Additionally, the dispensing configuration may be further defined by a tab that extends upwardly from the bottom surface. The tab may be configured to encourage the product to be removed generally vertically before being removed generally horizontally from the carton.

In some embodiments, the dispensing configuration is defined by the portion of the second end being removed to reveal a second portion of each product for dispensing. In some embodiments, the dispensing configuration is defined by the portion of the top surface being removed to reveal a third portion of each product for dispensing. In some embodiments, the dispensing configuration is defined by the portion of the first end being removed to reveal a first portion of each product for dispensing and the portion of the second end being removed to reveal a second portion of each product for dispensing. In some embodiments, the dispensing configuration is defined by the portion of the first end being removed to reveal a first portion of each product for dispensing, the portion of the second end being removed to reveal a second portion of each product for dispensing, and the portion of the top surface being removed to reveal a third portion of each product for dispensing.

In some embodiments, the carton further defines a front surface. Additionally, the first removable feature may be further associated with the front surface and positioned proximate the first end and the second removable feature may be further associated with the front surface and positioned proximate the second end.

In some embodiments, at least a portion of the first removable feature and at least a portion of the second removable feature are positioned adjacently to the third removable feature. In some embodiments, the first removable feature is defined within the top surface and a front surface to extend along a first plane, the second removable feature is defined within the top surface and the front surface to extend along a second plane, and the third removable feature is defined within the top surface to extend along a third plane. The first plane and the second plane may each be perpendicular to the third plane.

In some embodiments, in the closed configuration, the carton defines an enclosed volume configured to store the plurality of products therein for shipment purposes. In some embodiments, the first removable feature and the second removable feature each comprise a perforation. Additionally, the third removable feature may comprise a tear strip.

In another embodiment, a system that includes a plurality of products and a carton for dispensing and storing the plurality of products is provided. The carton defines a top surface, a bottom surface, a first end, and a second end. The carton comprises a first removable feature associated with the top surface and positioned proximate the first end. The first removable feature is configured to be selectively removed from the top surface to enable removal of a portion of the first end. The carton further comprises a second removable feature associated with the top surface and positioned proximate the second end. The second removable feature is configured to be selectively removed from the top surface to enable removal of a portion of the second end. The carton further comprises a third removable feature associated with the top surface and positioned between the first removable feature and the second removable feature. The third removable feature is configured to be selectively removed from the top surface to enable removal of a portion of the top surface. The carton further defines a closed configuration and a dispensing configuration. The dispensing configuration is defined by at least one of the portion of the first end being removed, the portion of the second end being removed, or the portion of the top surface being removed.

In some embodiments, the dispensing configuration is defined by the portion of the first end being removed to reveal a first portion of each product for dispensing.

In some embodiments, the system further comprises a basket configured to receive the carton. Additionally, the basket may further comprise at least one mounting structure.

In some embodiments, the basket defines a first wall, an opposing second wall, a front wall, and an opposing back wall. The front wall and back wall may each be spaced apart from the first wall and second wall to provide access to the first removable feature and second removable feature when the carton is in the closed configuration. The front wall and back wall may each be spaced apart from the first wall and second wall to provide access to a portion of each product when the carton is in the dispensing configuration.

In some embodiments, the basket defines a first wall and an opposing second wall. A portion of first wall and a portion of the second wall may each be defined to extend upwardly and outwardly so as to enable easy removal of each product when the carton is in the dispensing configuration.

In yet another embodiment, a method for manufacturing a carton for dispensing a plurality of products stored therein is provided. The method comprises providing a carton defining a top surface, a bottom surface, a first end, and a second end. The method further comprises defining a first removable feature within the top surface proximate the first end. The first removable feature is configured to be selectively removed from the top surface to enable removal of a portion of the first end. The method further comprises defining a second removable feature within the top surface proximate the second end. The second removable feature is configured to be selectively removed from the top surface to enable removal of a portion of the second end. The method further comprises defining a third removable feature within the top surface extending between the first removable feature and the second removable feature. The third removable feature is configured to be selectively removed from the top surface to enable removal of a portion of the top surface. The carton defines a closed configuration and a dispensing configuration. The dispensing configuration is defined by at least one of the portion of the first end being removed, the portion of the second end being removed, or the portion of the top surface being removed.

In some embodiments, the carton defines a front surface. The method further comprises defining the first removable feature by defining the first removable feature within a portion of the front surface proximate the first end. The method further comprises defining the second removable feature by defining the second removable feature within a portion of the front surface proximate the second end.

In some embodiments, the method further comprises defining the first removable feature by defining a perforation within the top surface, defining the second removable feature by defining a perforation within the top surface, and/or defining the third removable feature by defining a tear strip within the top surface.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

DETAILED DESCRIPTION OF THE INVENTION

Figure 1:
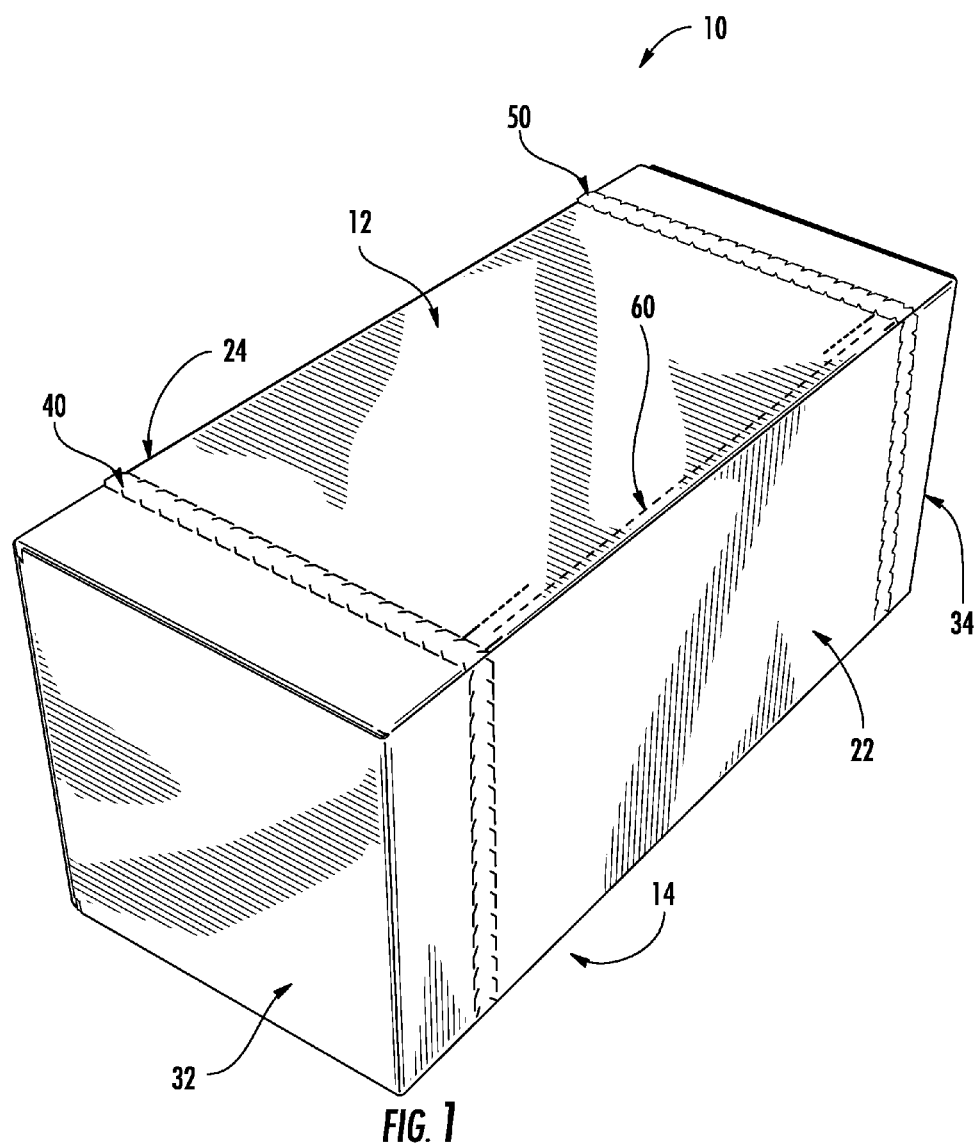
FIG. 1 is a perspective view of a carton, in accordance with example embodiments described herein.
Figure 2:
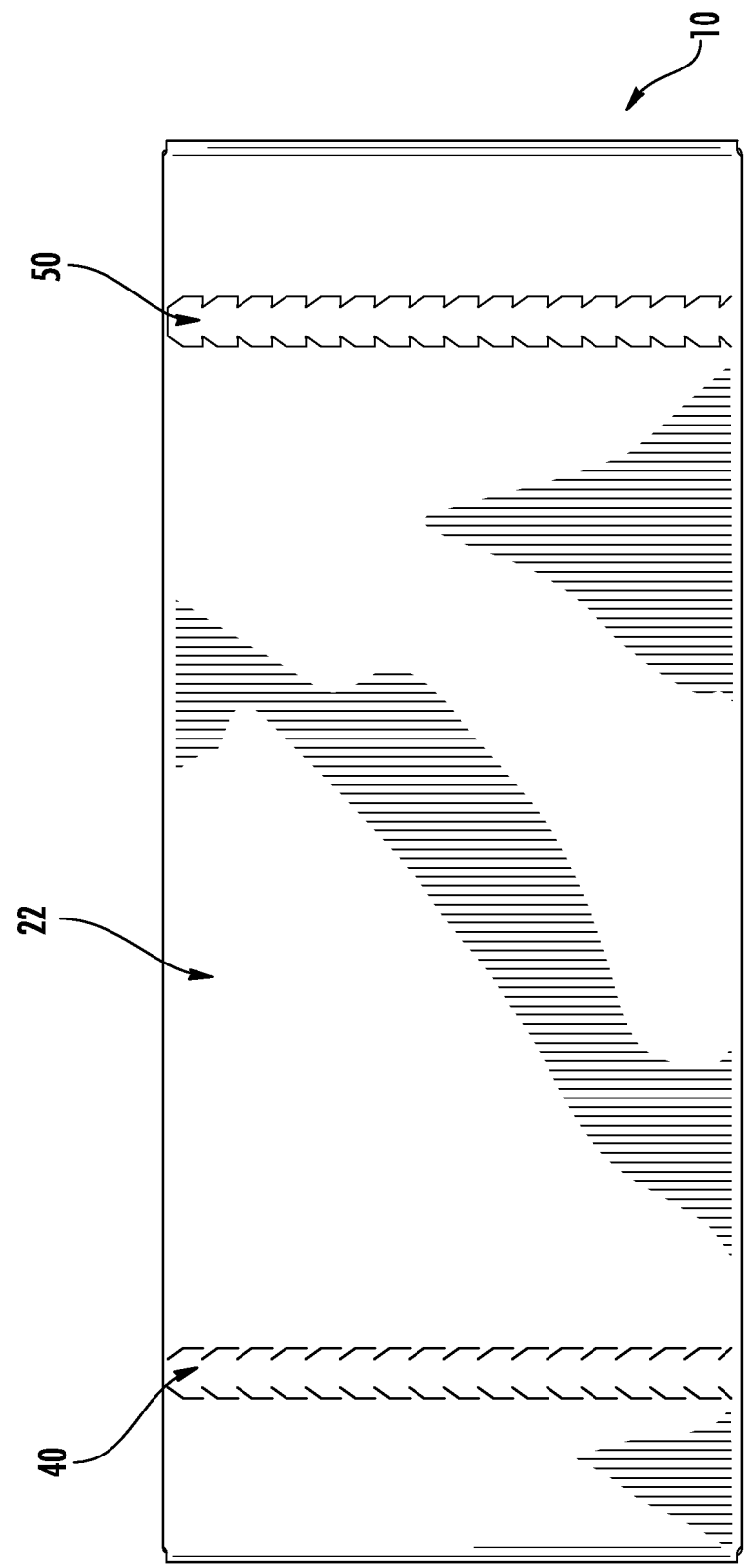
FIG. 2 is a front elevation view of the carton shown in FIG. 1, in accordance with example embodiments described herein.
Figure 3:
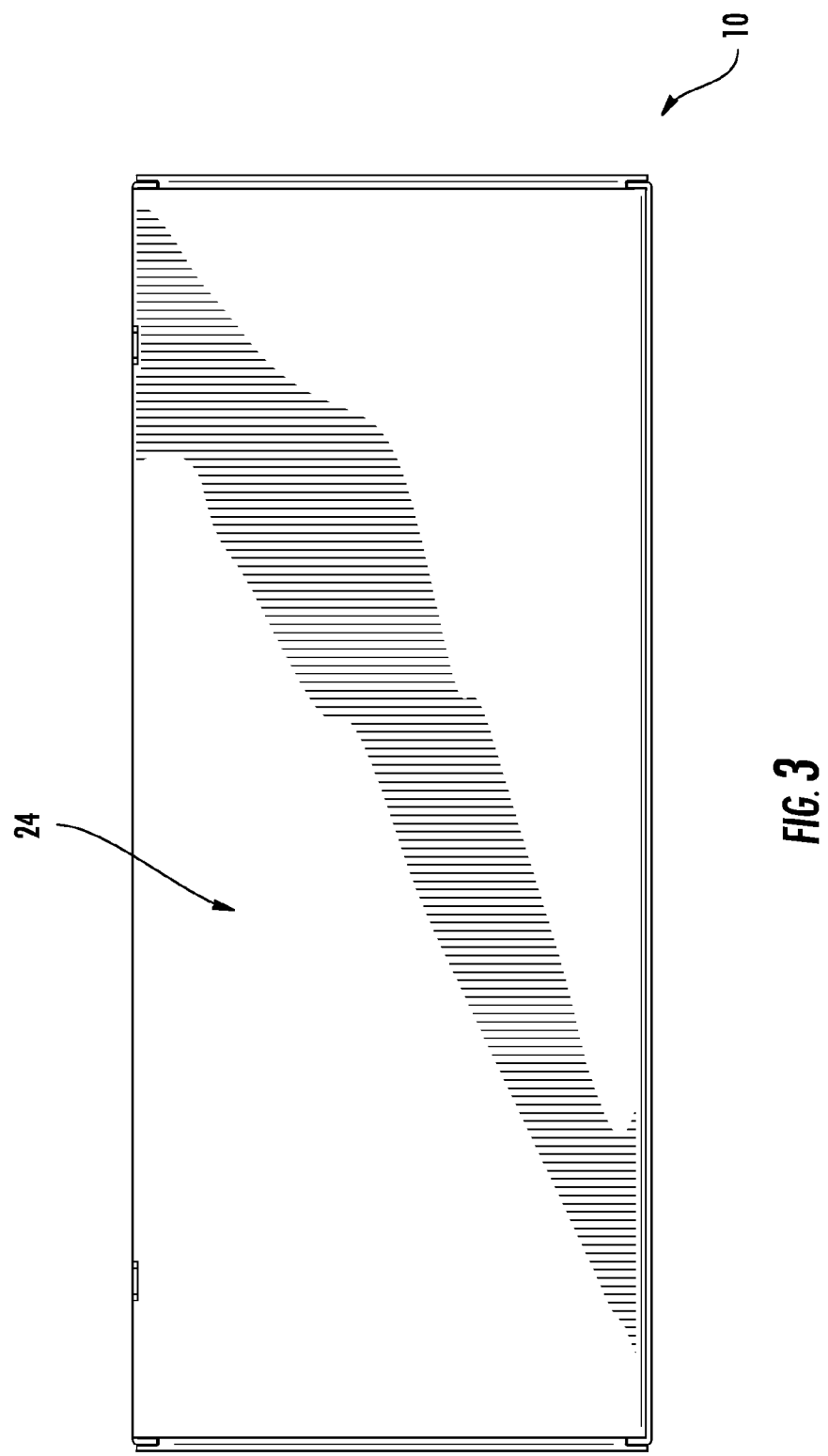
FIG. 3 is a rear elevation view of the carton shown in FIG. 1, in accordance with example embodiments described herein.
Figure 4:
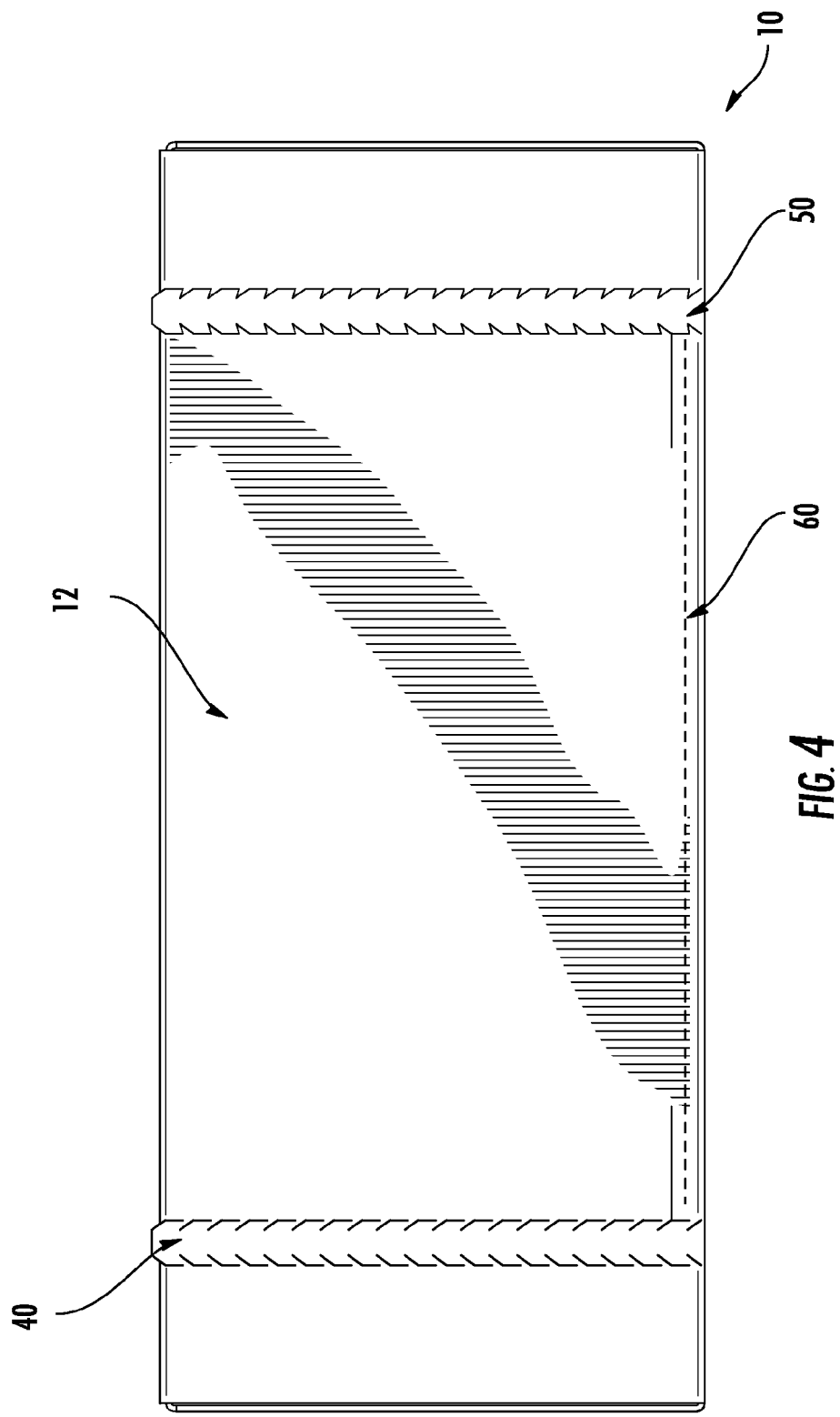
FIG. 4 is a top plan view of the carton shown in FIG. 1, in accordance with example embodiments described herein.
Figure 5:
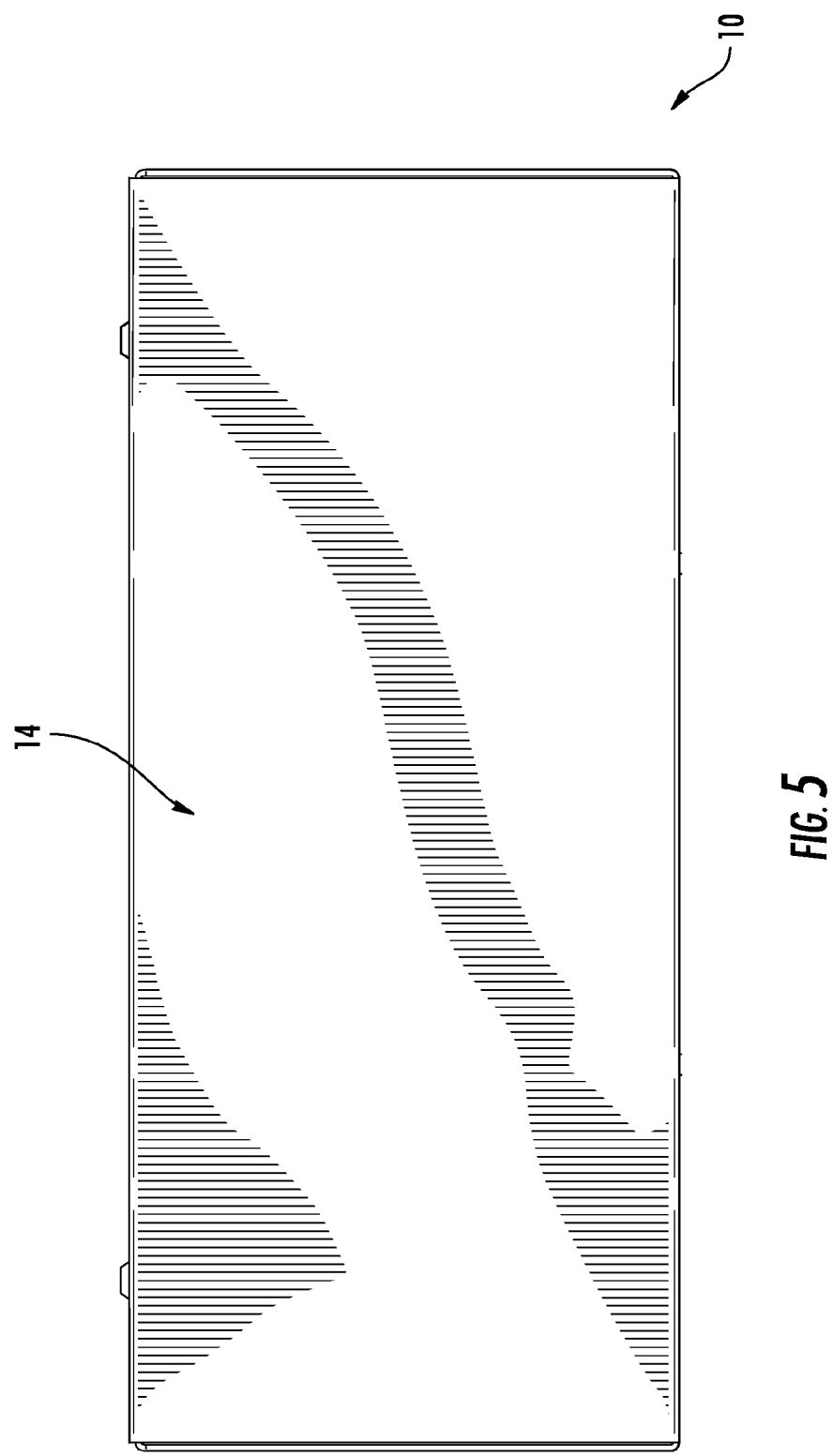
FIG. 5 is a bottom plan view of the carton shown in FIG. 1, in accordance with example embodiments described herein.
Figure 6:
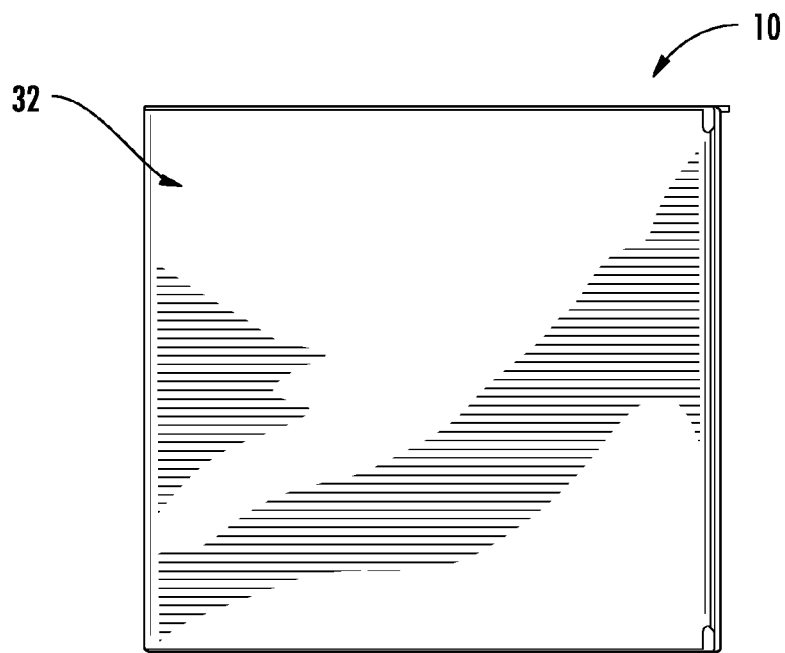
FIG. 6 is a left side elevation view of the carton shown in FIG. 1, in accordance with example embodiments described herein.
Figure 7:
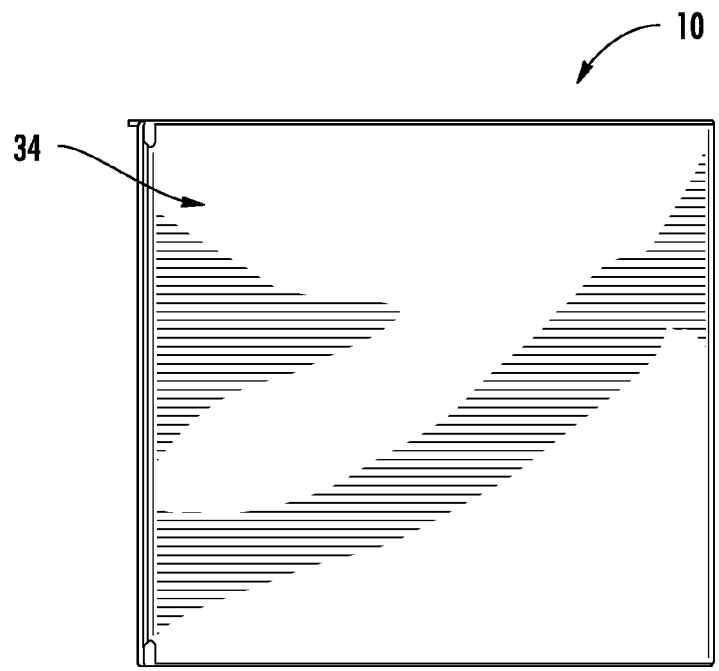
FIG. 7 is a right side elevation view of the carton shown in FIG. 1, in accordance with example embodiments described herein.

Exemplary embodiments of the present invention now will be described more fully hereinafter with reference to the accompanying drawings, in which some, but not all embodiments of the invention are shown. Indeed, the invention may be embodied in many different forms and should not be construed as limited to the exemplary embodiments set forth herein; rather, these embodiments are provided so that this disclosure will satisfy applicable legal requirements. Like reference numerals refer to like elements throughout.

Figure 9:
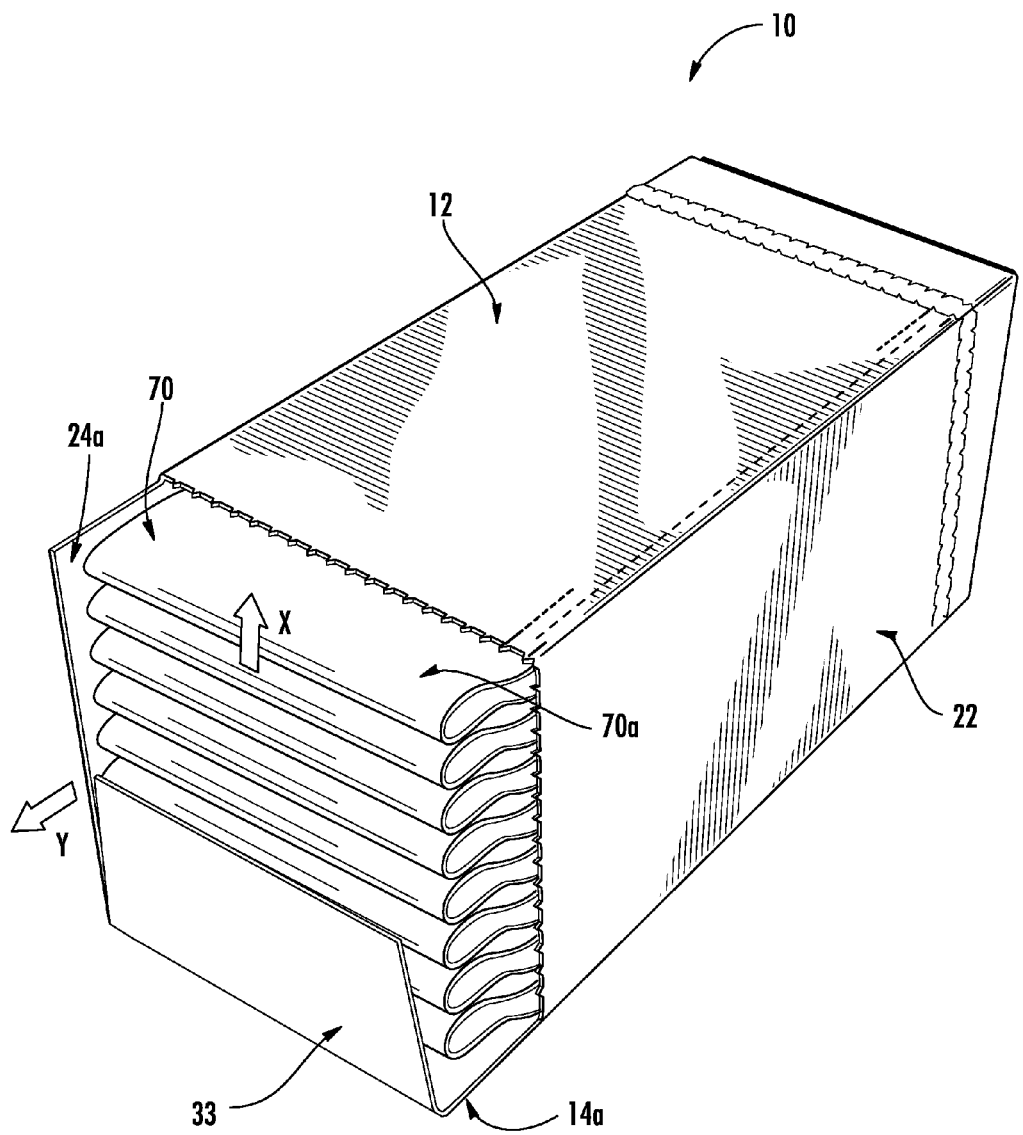
FIG. 9 is a perspective view of the carton shown in FIG. 1, wherein a portion of the left end of the carton has been removed to form a dispensing configuration for the product stored therein, in accordance with example embodiments described herein.

FIG. 1 shows an example carton 10 for storing and dispensing a plurality of products according to some embodiments of the present invention. The carton 10 defines a top surface 12 and an opposing bottom surface 14. The carton further defines a first end 32 and an opposing second end 34. Additionally, the carton 10 defines a front surface 22 and an opposing back surface 24. As shown in FIGS. 1-7, the carton 10 defines a closed configuration such that the top surface 12, bottom surface 14, first end 32, second end 34, front surface 22, and back surface 24 define an enclosed volume configured to store the plurality of products (shown, for example, in FIG. 9) for shipment purposes.

The carton 10 may be made of any material (e.g., paper board, cardboard, plastic, etc.). In some embodiments, at least some portions of the carton 10 may be defined so as to be removed from the carton 10. For example, with reference to FIG. 1, the carton 10 may define one or more removable features. As used herein, a removable feature may define any feature that is configured to be removed from the carton (e.g., via a perforation, a tear strip, knife cuts, etc.) to enable separation of a portion of the carton with respect to the remainder of the carton. In some embodiments, the carton 10 may comprise material capable of being removed (e.g., torn) so as to facilitate removal of the one or more removable features.

In some embodiments, the carton comprises a first removable feature associated with the top surface and positioned proximate the first end. In some embodiments, the first removable feature is further associated with the front surface and positioned proximate the first end. For example, with reference to FIG. 1, the carton 10 comprises a first removable feature 40 defined within the top surface 12 and the front surface 22 proximate the first end 32.

Additionally, in some embodiments, the carton comprises a second removable feature associated with the top surface and positioned proximate the second end. In some embodiments, the second removable feature is further associated with the front surface and positioned proximate the second end. For example, with reference to FIG. 1, the carton 10 comprises a second removable feature 50 defined within the top surface 12 and the front surface 22 proximate the second end 34.

Additionally, in some embodiments, the carton comprises a third removable feature associated with the top surface and positioned between the first removable feature and the second removable feature. For example, with reference to FIG. 1, the carton 10 comprises a third removable feature 60 defined within the top surface 12 extending generally between the first removable feature 40 and the second removable feature 50.

Figure 8:
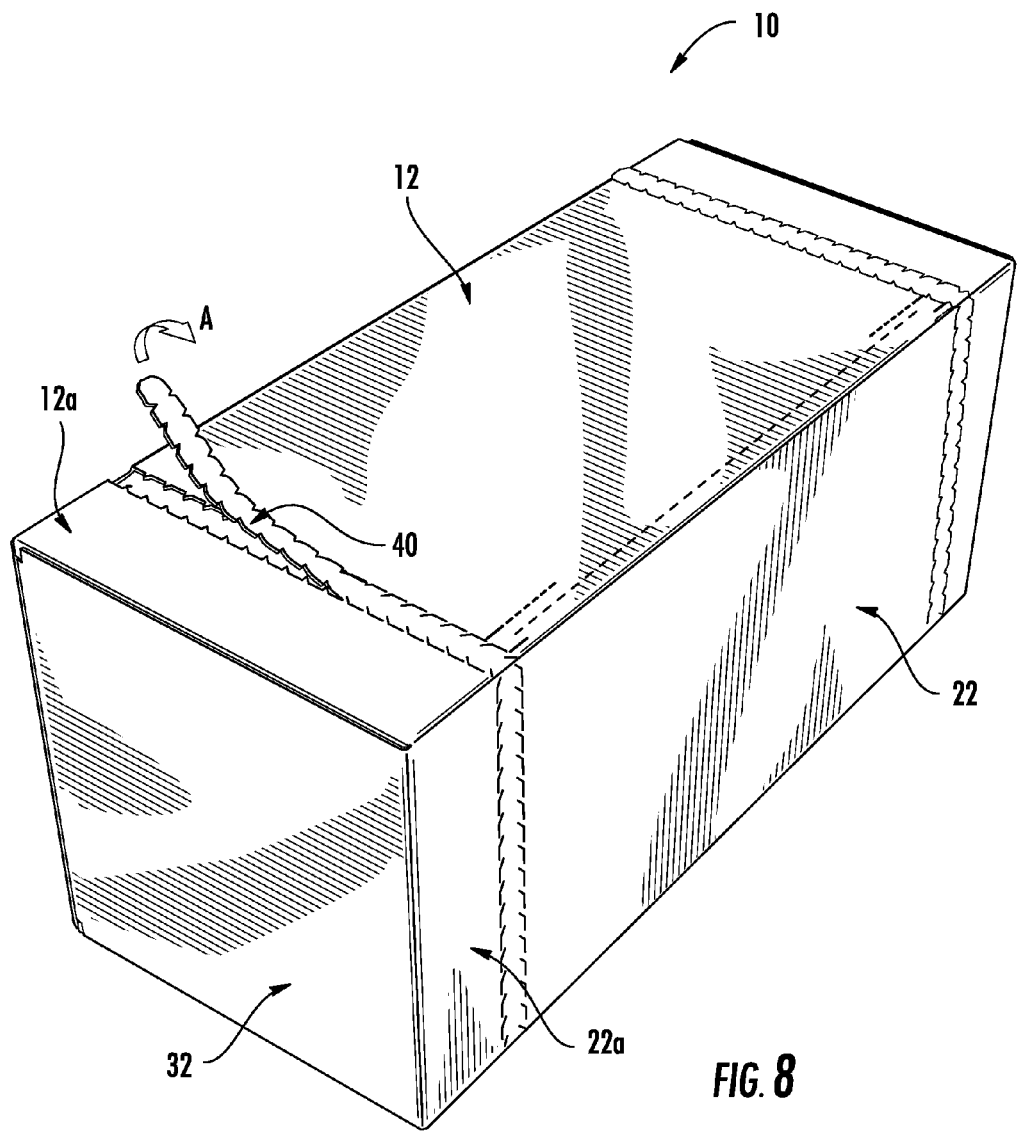
FIG. 8 is a perspective view of the carton shown in FIG. 1, wherein a first removable feature has been partially removed, in accordance with example embodiments described herein.

In some embodiments, the first removable feature is configured to be selectively removed from the top surface to enable removal of a portion of the first end. For example, with reference to FIG. 8, the first removable feature 40 may be configured to be removed from the top surface 12, such as represented by arrow A. In the depicted embodiment, the first removable feature 40 comprises a perforation defined within the top surface 12 of the carton 10. While the depicted embodiment details a perforation comprising two parallel lines of perforations, other configurations are contemplated, such as a single line of perforations, a tear strip, a line of weakness, etc.

As the first removable feature 40 is removed from the top surface 12, a first portion 12a of the top surface 12 is separated from the remainder of the top surface 12. Additionally, as noted herein, the first removable feature 40 may be defined within the front surface 22. In such an embodiment, the first removable feature 40 may also be removed from the front surface 22 so as to separate a first portion 22a of the front surface 22 from the remainder of the front surface 22.

With the first removable feature 40 removed from the carton 10, a portion of the first end 32 may be removed from the carton 10. For example, with reference to FIG. 8, the first portion 12a of the top surface 12, the first portion 22a of the front surface 22, and a portion of the first end 32 may be removed to form a first dispensing configuration of the carton 10 (shown in FIG. 9). In the depicted embodiment of FIG. 9, the first dispensing configuration is defined by the portion of the first end 32 being removed to reveal a first portion 70a of each of a plurality of products 70.

As noted herein, example embodiments of the carton may be used for shipping and dispensing a particular product, such as blood pressure cuffs. As also noted herein, it may be beneficial to prevent contamination of each disposable blood pressure cuff. As such, in some embodiments, it may be desirable to maintain certain support structures to maintain rigidity of the carton in the dispensing configuration and also to provide a barrier to prevent contamination of the products being dispensed by minimizing exposure of the products (e.g., blood pressure cuffs) to the external environment. Thus, in some embodiments, the first dispensing configuration may be further defined by the first portion of each product being supported by the bottom surface and the back surface of the carton. For example, with reference to FIG. 9, once the portion of the first end 32 has been removed, a first portion 24a of the back surface 24 and a first portion 14a of the bottom surface 14 remain to provide support for the first portion 70a of each of the plurality of products 70.

Further, as noted herein, it may also be beneficial to prevent contamination of the disposable blood pressure cuffs during dispensing. In particular, adjacent cuffs can easily become stuck together during dispensing, which may cause a second cuff to be dispensed from the carton. By prematurely dispensing the cuff, that cuff becomes more prone to contamination from the external environment. As such, some embodiments seek to encourage removal of only one product at a time. Indeed, one possible product, disposable blood pressure cuffs, commonly has a number of irregular surfaces (e.g., ports, tubes, and attachment surfaces) that may engage adjacent cuffs. As such, the orientation of the cuffs within the carton is important to facilitate dispensing one cuff at a time. Thus, some embodiments of the carton encourage packaging of the cuffs horizontally along their length. Further, some embodiments contemplate one or more of the dispensing configurations of the carton defining a vertical surface (e.g., a tab) at an end of the carton, thereby requiring a user to initially lift an end of the cuff vertically prior to removing the cuff in a horizontal direction. This process is designed to promote disengagement between the cuff being removed and an adjacent cuff.

Thus, in some embodiments, the dispensing configuration is further defined by a tab that extends upwardly from the bottom surface. The tab is configured to encourage the product to be removed generally vertically before being removed generally horizontally from the carton to encourage removal of only one product at a time. For example, with reference to FIG. 9, a tab 33 remains after removal of the portion of the first end 32. The tab 33 extends upwardly from an edge of the first portion 14a of the bottom surface 14. The tab 33 is designed to encourage removal of the product vertically (e.g., along arrow X) and then horizontally (e.g., along arrow Y). Such a motion may encourage removal of only one product at a time.

Figure 10:
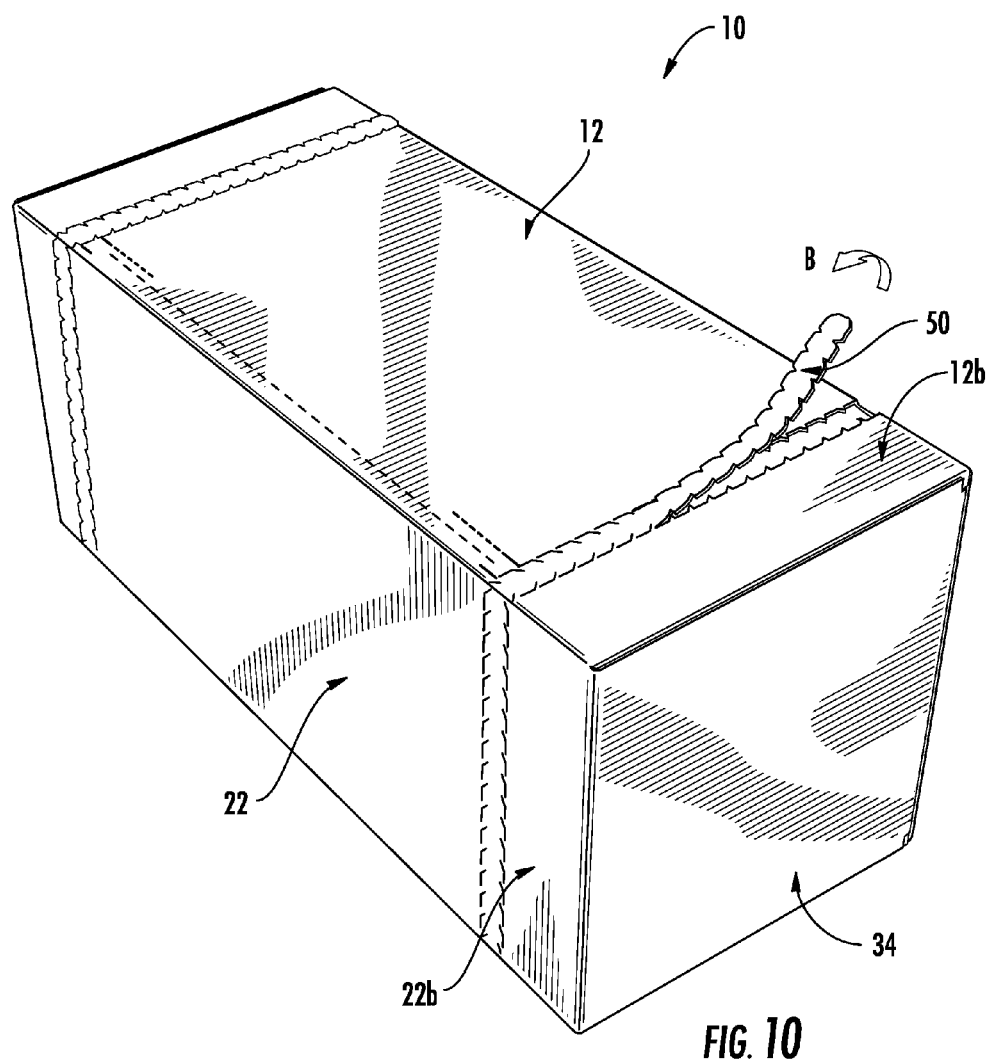
FIG. 10 is a perspective view of the carton shown in FIG. 1, wherein a second removable feature has been partially removed, in accordance with example embodiments described herein.

In some embodiments, the second removable feature is configured to be selectively removed from the top surface to enable removal of a portion of the second end. For example, with reference to FIG. 10, the second removable feature 50 may be configured to be removed from the top surface 12, such as represented by arrow B. In the depicted embodiment, the second removable feature 50 comprises a perforation defined within the top surface 12 of the carton 10. While the depicted embodiment details a perforation comprising two parallel lines of perforations, other configurations are contemplated, such as a single line of perforations, a tear strip, a line of weakness, etc.

As the second removable feature 50 is removed from the top surface 12, a second portion 12b of the top surface 12 may be separated from the remainder of the top surface 12. Additionally, as noted herein, the second removable feature 50 may be defined within the front surface 22. In such an embodiment, the second removable feature 50 may also be removed from the front surface 22 so as to separate a second portion 22b of the front surface 22 from the remainder of the front surface 22.

Figure 11:
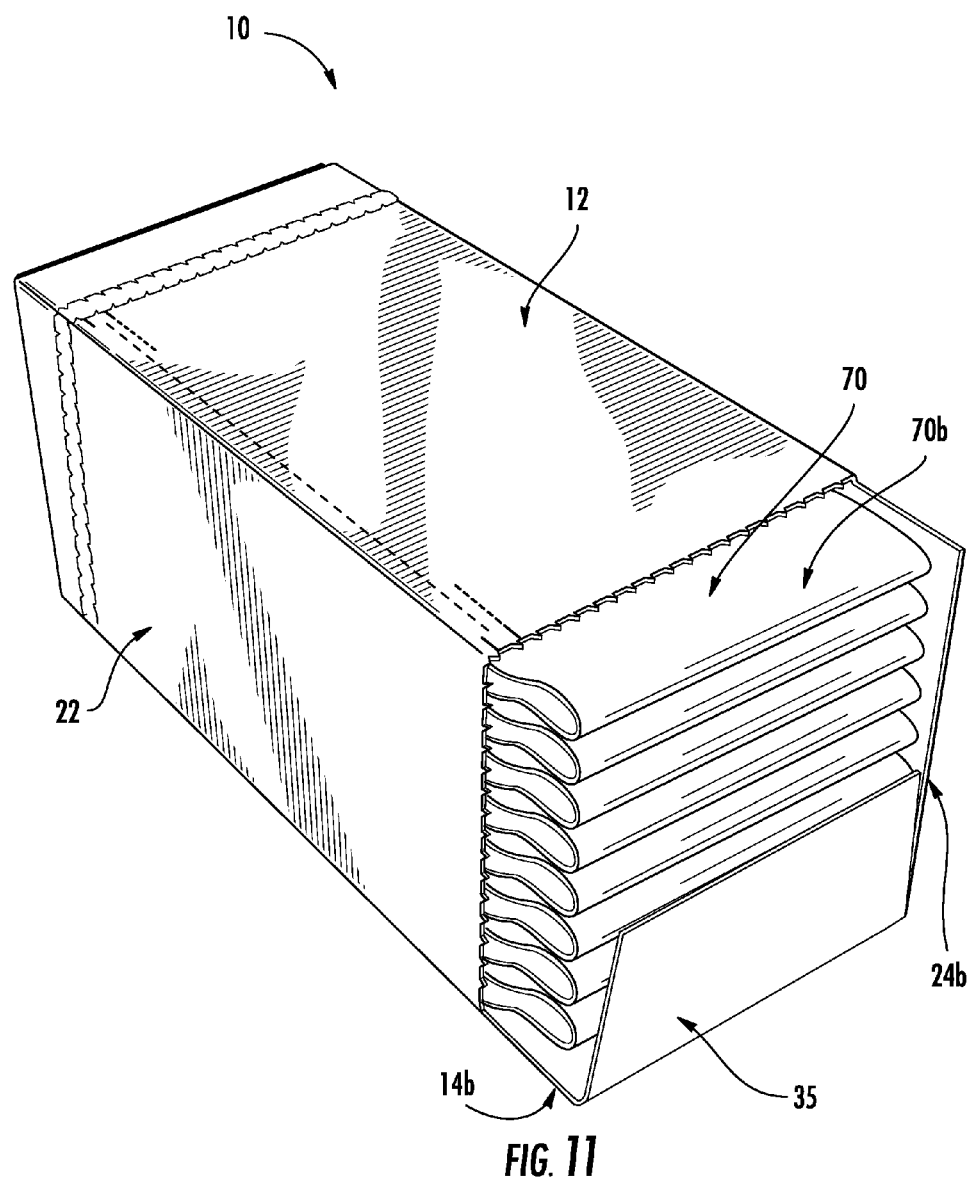
FIG. 11 is a perspective view of the carton shown in FIG. 1, wherein a portion of the right end of the carton has been removed to form another dispensing configuration for the product stored therein, in accordance with example embodiments described herein.

With the second removable feature 50 removed from the carton 10 a portion of the second end 34 may be removed from the carton 10. For example, with reference to FIG. 10, the second portion 12b of the top surface 12, the second portion 22b of the front surface 22, and a portion of the second end 34 may be removed to form a second dispensing configuration of the carton 10 (shown in FIG. 11). In the depicted embodiment of FIG. 11, the second dispensing configuration is defined by the portion of the second end 34 being removed to reveal a second portion 70b of each of a plurality of products 70.

Additionally, in some embodiments, such as to maintain rigidity of the carton and/or prevent contamination of the disposable blood pressure cuffs, the second dispensing configuration may be further defined by the second portion of each product being supported by the bottom surface and the back surface of the carton. For example, with reference to FIG. 11, once the portion of the second end 34 has been removed, a second portion 24b of the back surface 24 and a second portion of the bottom surface 14b remain to provide support for the second portion 70b of each of the plurality of products 70.

Additionally, in some embodiments, such as to prevent contamination of the disposable blood pressure cuffs during dispensing, the dispensing configuration may be further defined by a tab that extends upwardly from the bottom surface. The tab is configured to encourage the product to be removed generally vertically before being removed generally horizontally from the carton to encourage removal of only one product at a time. For example, with reference to FIG. 11, a tab 35 remains after removal of the portion of the second end 34. The tab 35 extends upwardly from an edge of the second portion 14b of the bottom surface 14. Similar to the tab 33 (shown in FIG. 9), the tab 35 may be designed to encourage removal of the product vertically and then horizontally. Such a motion may encourage removal of only one product at a time.

Figure 12:
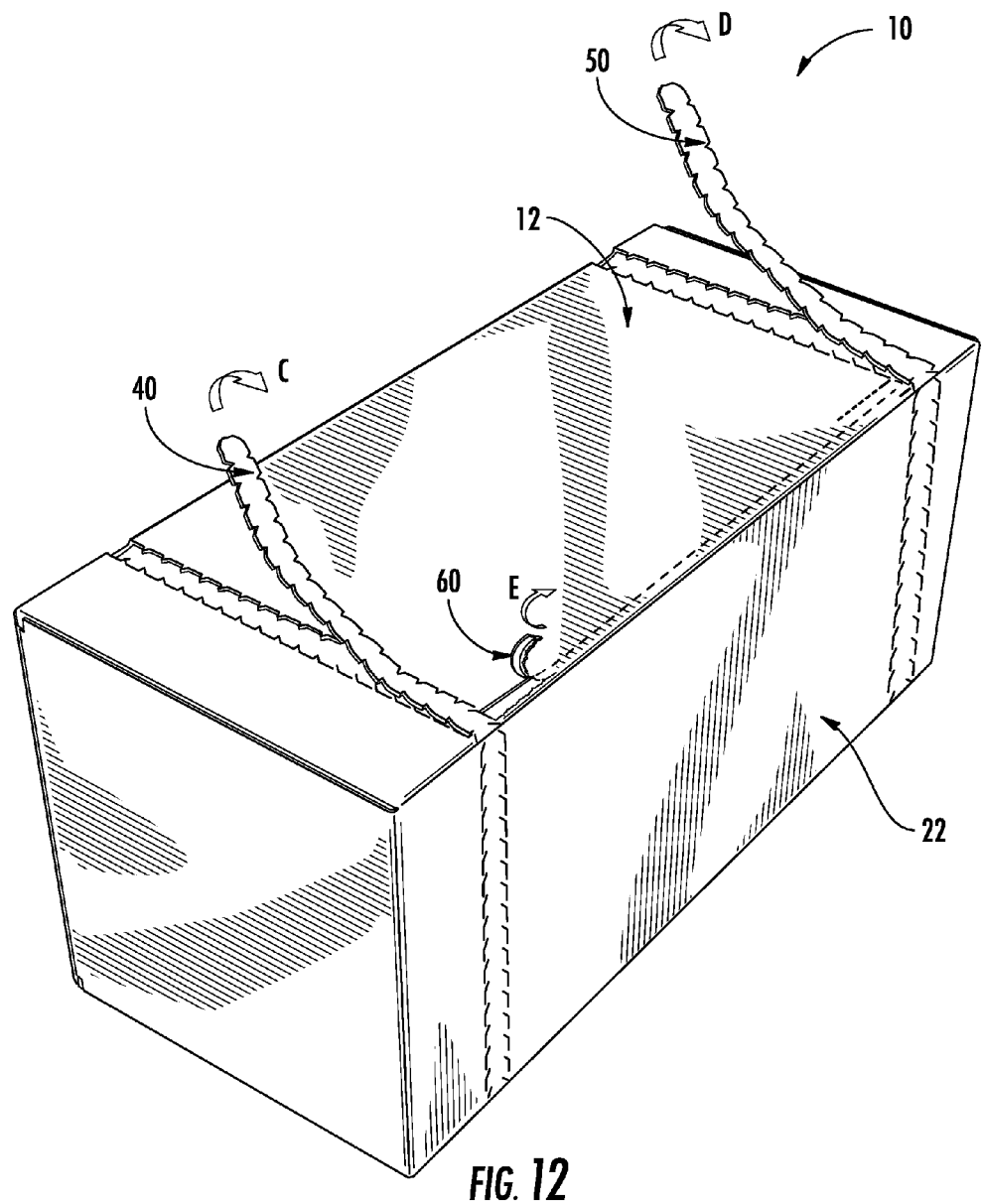
FIG. 12 is a perspective view of the carton shown in FIG. 1, wherein a first removable feature, a second removable feature, and a third removable feature have each been partially removed, in accordance with example embodiments described herein.

In some embodiments, a third removable feature is configured to be selectively removed from the top surface to enable removal of a portion of the top surface. For example, with reference to FIG. 12, the third removable feature 60 may be configured to be removed from the top surface 12, such as represented by arrow E. In the depicted embodiment, the third removable feature 60 comprises a tear strip defined within the top surface 12 of the carton 10.

Figure 13:
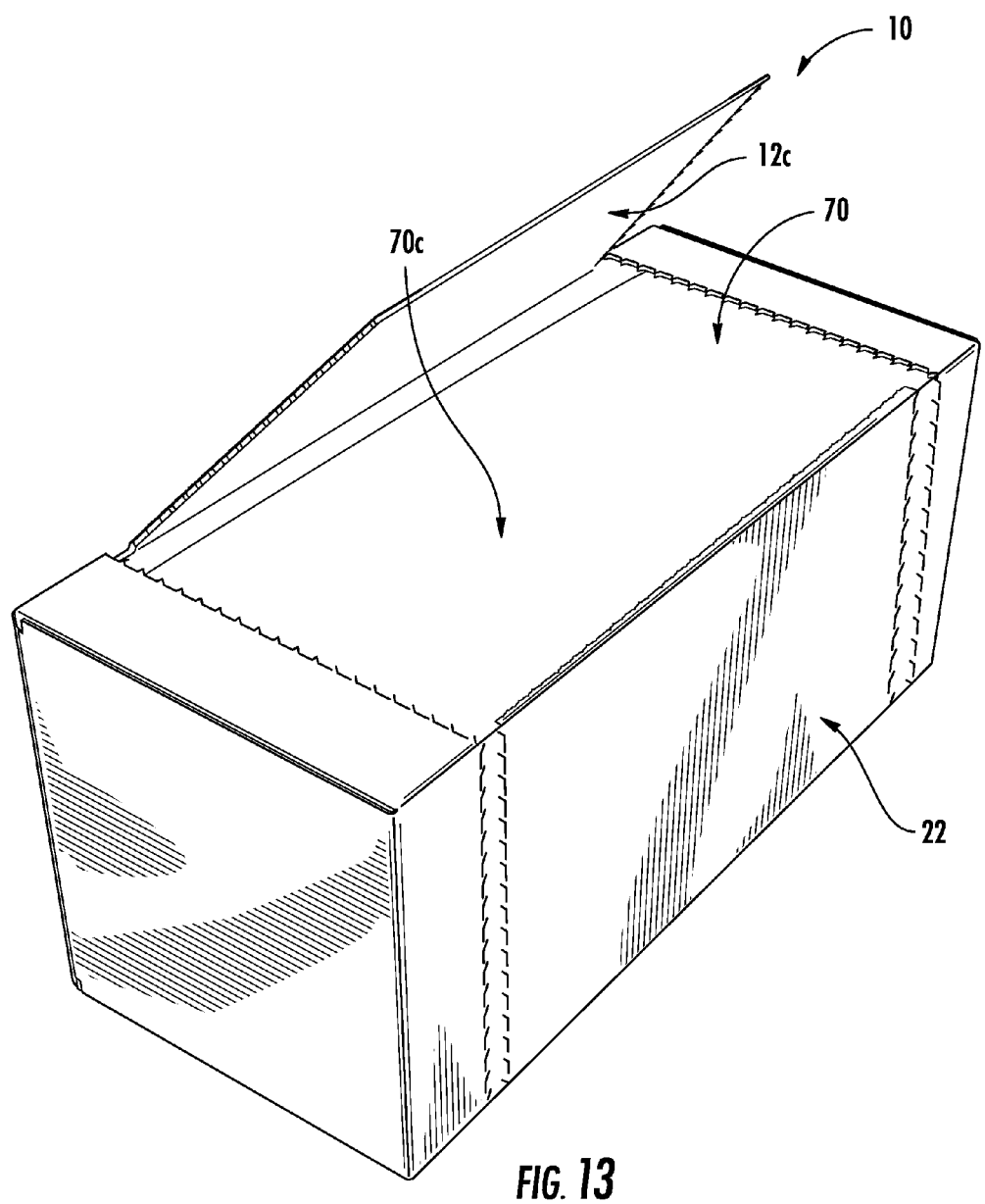
FIG. 13 is a perspective view of the carton shown in FIG. 1, wherein a portion of the top surface of the carton has been removed to form another dispensing configuration for the product stored therein, in accordance with example embodiments described herein.

As the third removable feature 60 is removed from the top surface 12, a third portion 12c of the top surface 12 may be separated from the remainder of the top surface 12 (shown in FIG. 13). Additionally or alternatively, the first removable feature 40 and/or the second removable feature 50 may be defined within the top surface 12 relative to the third removable feature 60 to enable removal of the third removable feature 60. For example, removal of the first removable feature 40 from the top surface 12 (e.g., along arrow C) and removal of the second removable feature 50 from the top surface 12 (e.g., along arrow D) may enable removal of the third removable feature 60, such as by enabling a user to access and pull on an end of the third removable feature. Thus, removal of the first removable feature 40, second removable feature 50, and third removable feature 60 from the top surface 12 may cause the third portion 12c of the top surface 12 to be separated from the remainder of the top surface 12, such as for removal therefrom.

With the third removable feature 60 removed from the carton 10, a portion of the top surface 12 may be removed from the carton 10. For example, with reference to FIG. 13, the third portion 12c of the top surface 12 may be positioned away from the products or removed relative to the carton to form a third dispensing configuration (shown in FIG. 13). For example, in some embodiments, the third portion 12c may be positioned away (e.g., peeled away) from the products by the user to allow for dispensing. Alternatively, the third portion 12c (or a portion thereof) may be completely removed from the carton 10 by the user, such as by being torn or ripped off. In the depicted embodiment of FIG. 13, the third dispensing configuration is defined by the portion of the top surface 12 being removed to reveal a third portion 70c of each of a plurality of products 70.

As such, in some embodiments, such as those described above, the carton 10 may be configured to be selectively formed into dispensing configurations that are suited for a particular user. In such a manner, in some embodiments, the dispensing configuration of the carton may be defined by at least one of the portion of the first end being removed, the portion of the second end being removed, and/or the portion of the top surface being removed.

In some embodiments, to aid in formation of certain dispensing configurations, the removable features of the carton may be configured in certain positions with respect to each other. For example, in some embodiments, with reference to FIG. 1, at least a portion of the first removable feature 40 and at least a portion of the second removable feature 50 may be defined within the top surface 12 adjacent to the third removable feature 60. Additionally or alternatively, in some embodiments, the first removable feature 40 may be defined within the top surface 12 and the front surface 22 to extend along a first plane proximate the first end 32. Additionally, the second removable feature 50 may be defined within the top surface 12 and the front surface 22 to extend along a second plane proximate the second end 34. In such an embodiment, the third removable feature 60 may be defined within the top surface 12 to extend along a third plane that is perpendicular to the first plane and the second plane. Additionally, the third removable feature 60 may extend at one end from the first plane to a second end at the second plane. In such a manner, similar to some embodiments noted herein, partial removal of the first removable feature 40 and the second removable feature 50 may enable easy access to the perpendicular third removable feature 60.

Though the above described embodiments detail examples that include the first removable feature and second removable feature each comprising a perforation and the third removable feature comprising a tear strip, some embodiments of the present invention contemplate other configurations of features capable of being removed (e.g., the third removable feature may comprise a perforation, the first removable feature may define a tear strip, the third removable feature may define knife cuts, etc.). Along these same lines, although in some example embodiments described herein the first removable feature, second removable feature, and third removable feature are defined within the top surface and in certain configurations with respect to each other, other configurations are contemplated. For example, at least one of the first removable feature, second removable feature, and third removable feature may be defined in a different manner (e.g., a straight line, a curved line, etc.). Likewise, at least one of the first removable feature, second removable feature, and third removable feature may be defined such that only a portion may need to be removed to enable separation of a portion of the carton from the remainder of the carton. Further, more or fewer than three different removable features are also contemplated by some embodiments of the present invention.

Figure 14:
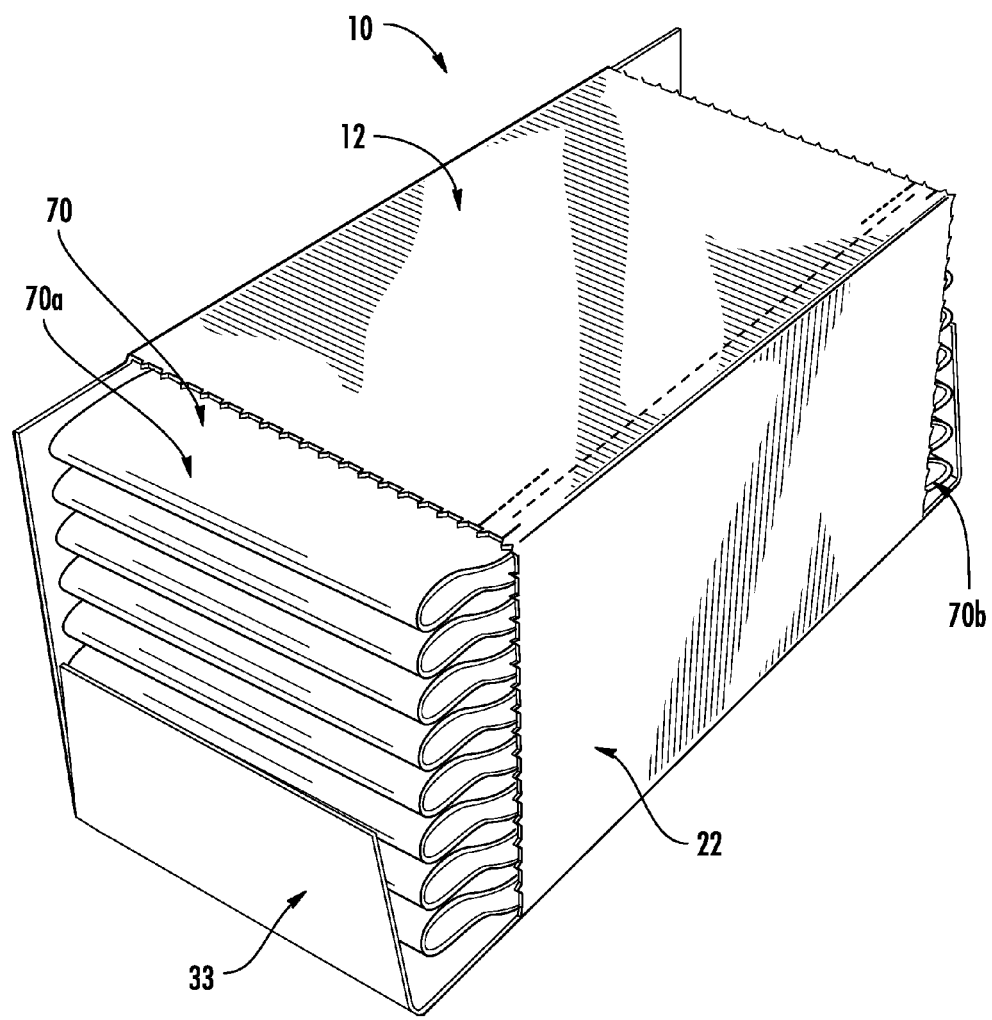
FIG. 14 is a perspective view of the carton shown in FIG. 1, wherein a portion of the right end of the carton and a portion of the left end of the carton have been removed to form another dispensing configuration for the product stored therein, in accordance with example embodiments described herein.
Figure 15:
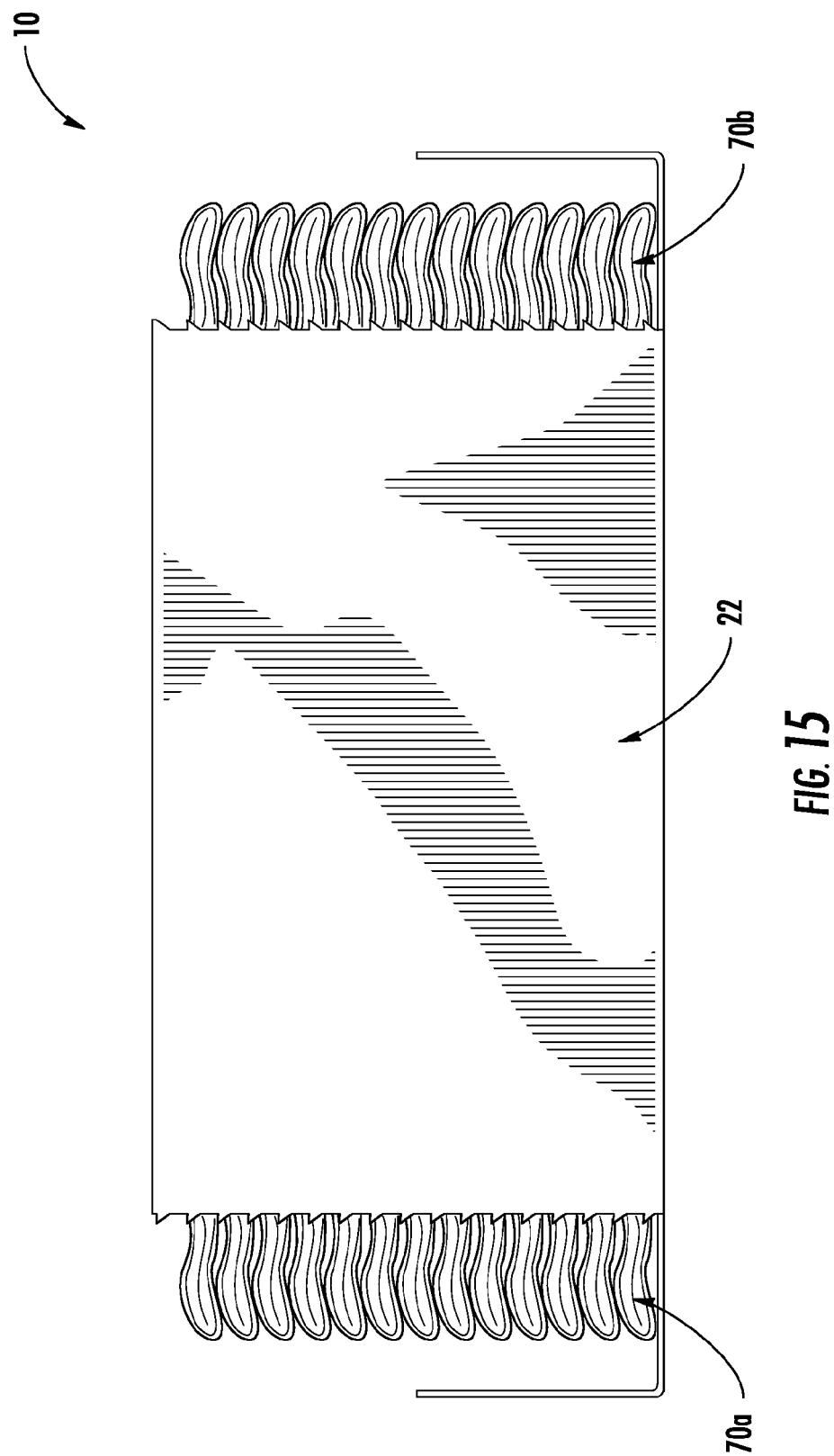
FIG. 15 is a front elevation view of the carton shown in FIG. 14, in accordance with example embodiments described herein.

In some embodiments, the carton may be configured to selectively form other dispensing configurations. For example, with reference to FIGS. 14 and 15, the carton 10 may form a fourth dispensing configuration defined by the portion of the first end 32 being removed to reveal a first portion 70a of each of the plurality of products 70 for dispensing and the portion of the second end 34 being removed to reveal a second portion 70b of each of the plurality of products 70 for dispensing. In such a fourth dispensing configuration, the product 70 may be dispensed from either the first end 32 or the second end 34 of the carton 10.

Figure 16:
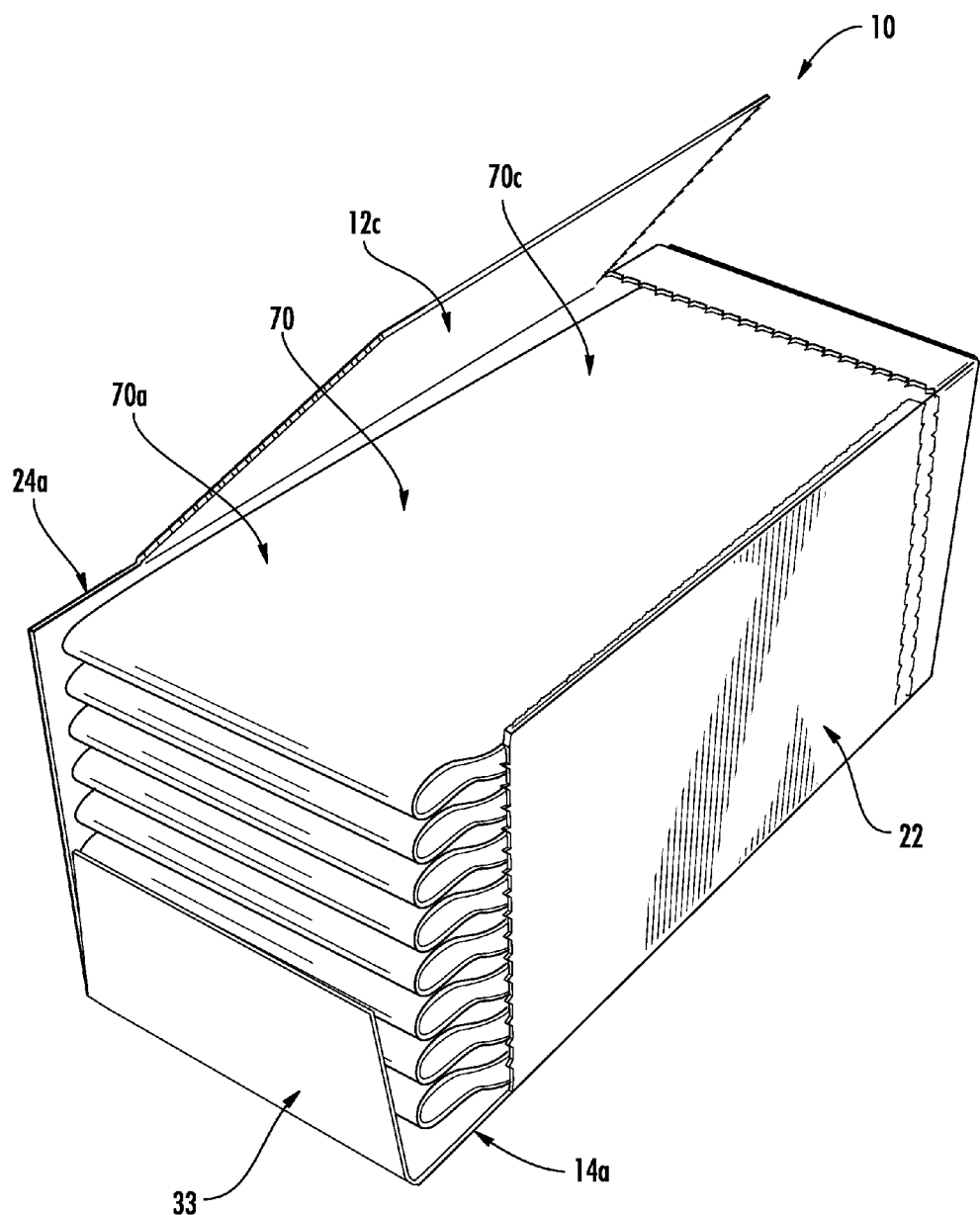
FIG. 16 is a perspective view of the carton shown in FIG. 1, wherein a portion of the left end of the carton and a portion of the top surface of the carton have been removed to form another dispensing configuration for the product stored therein, in accordance with example embodiments described herein.

Another example dispensing configuration for the carton is illustrated in FIG. 16. In the depicted embodiment, the carton 10 forms a fifth dispensing configuration defined by the portion of the first end 32 (shown in FIG. 1) being removed to reveal a first portion 70a of each of the plurality of products 70 for dispensing and the portion 12c of the top surface 12 being removed to reveal a third portion 70c of each of the plurality of products 70 for dispensing. In such a fifth dispensing configuration, the product 70 may be dispensed from either the first end 32 or the top of the carton 10, or a combination of the first end 32 and the top of the carton 10.

Figure 17:
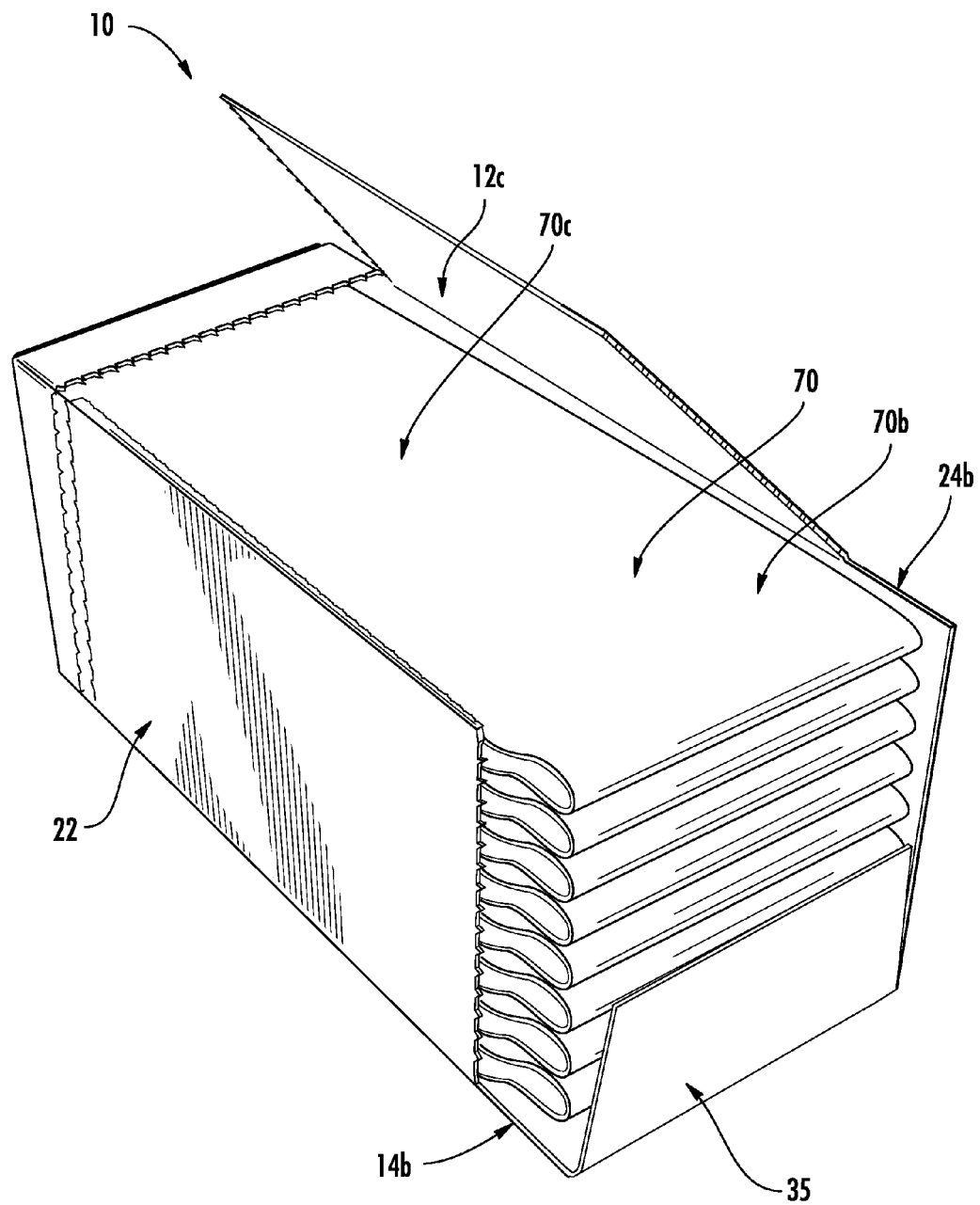
FIG. 17 is a perspective view of the carton shown in FIG. 1, wherein a portion of the right end of the carton and a portion of the top surface of the carton have each been removed to form another dispensing configuration for the product stored therein, in accordance with example embodiments described herein.

A further example dispensing configuration for the carton is illustrated in FIG. 17. In the depicted embodiment, the carton 10 forms a sixth dispensing configuration defined by the portion of the second end 34 (shown in FIG. 1) being removed to reveal a second portion 70b of each of the plurality of products 70 for dispensing and the portion 12c of the top surface 12 being removed to reveal a third portion 70c of each of the plurality of products 70 for dispensing. In such a sixth dispensing configuration, the product 70 may be dispensed from either the second end 34 or the top of the carton 10, or a combination of the second end 34 and the top of the carton 10.

Figure 18:
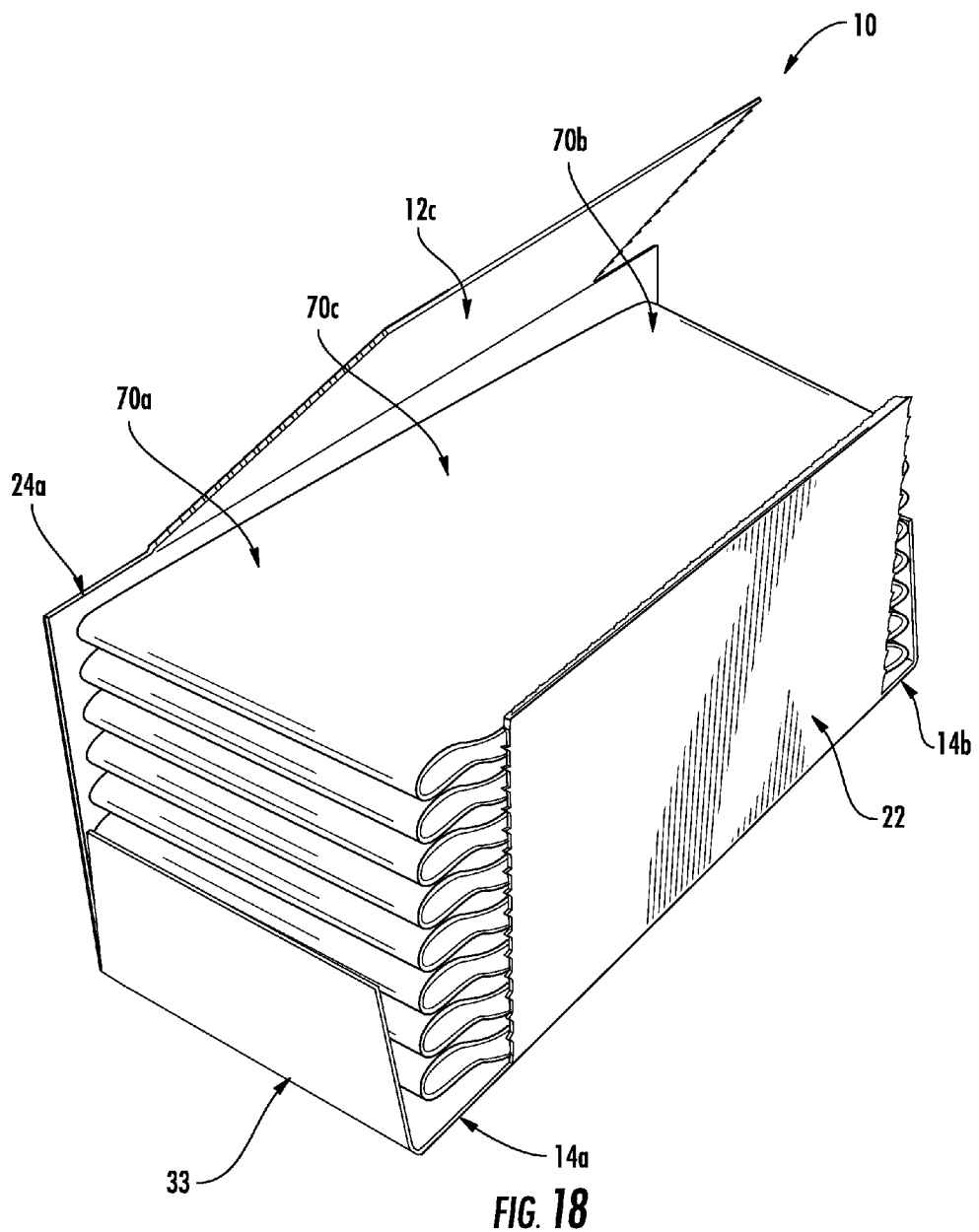
FIG. 18 is a perspective view of the carton shown in FIG. 1, wherein a portion of the right end of the carton, a portion of the left end of the carton, and a portion of the top surface of the carton have each been removed to form another dispensing configuration for the product stored therein, in accordance with example embodiments described herein.

Another example dispensing configuration for the carton is illustrated in FIG. 18. In the depicted embodiment, the carton 10 forms a seventh dispensing configuration defined by the portion of the first end 32 (shown in FIG. 1) being removed to reveal a first portion 70a of each of the plurality of products 70 for dispensing, the portion of the second end 34 being removed to reveal a second portion 70b of each of the plurality of products 70 for dispensing, and the portion 12c of the top surface 12 being removed to reveal a third portion 70c of each of the plurality of products 70 for dispensing. In such a seventh dispensing configuration, the product 70 may be dispensed from any of the first end 32, the second end 34, or the top of the carton 10, or any combination thereof.

In some embodiments, a system for shipping and dispensing products is provided. The system may comprise a plurality of products and a carton for storing the plurality of products. The carton may be embodied as define any example carton described herein, such as carton 10.

Figure 19:
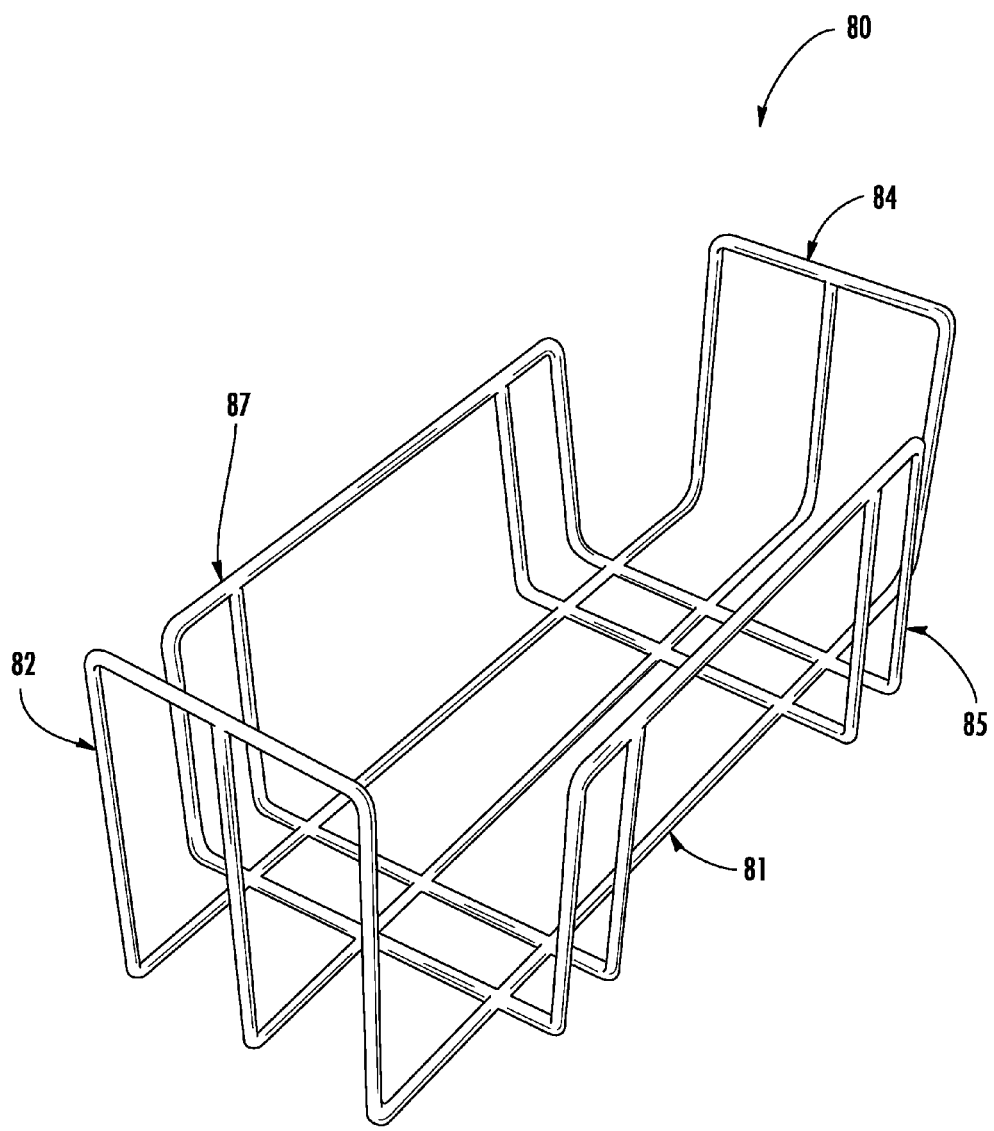
FIG. 19 is a perspective view of a basket for holding the carton shown in FIG. 1, in accordance with example embodiments described herein.

In some embodiments, the system may further comprise a basket configured to receive the carton. With reference to FIG. 19, the basket 80 may define a bottom 81, a first wall 82, an opposing second wall 84, a front wall 85, and an opposing back wall 87. As shown in FIG. 19, each wall (e.g., front wall 85) may be defined by one or more wires.

Figure 20:
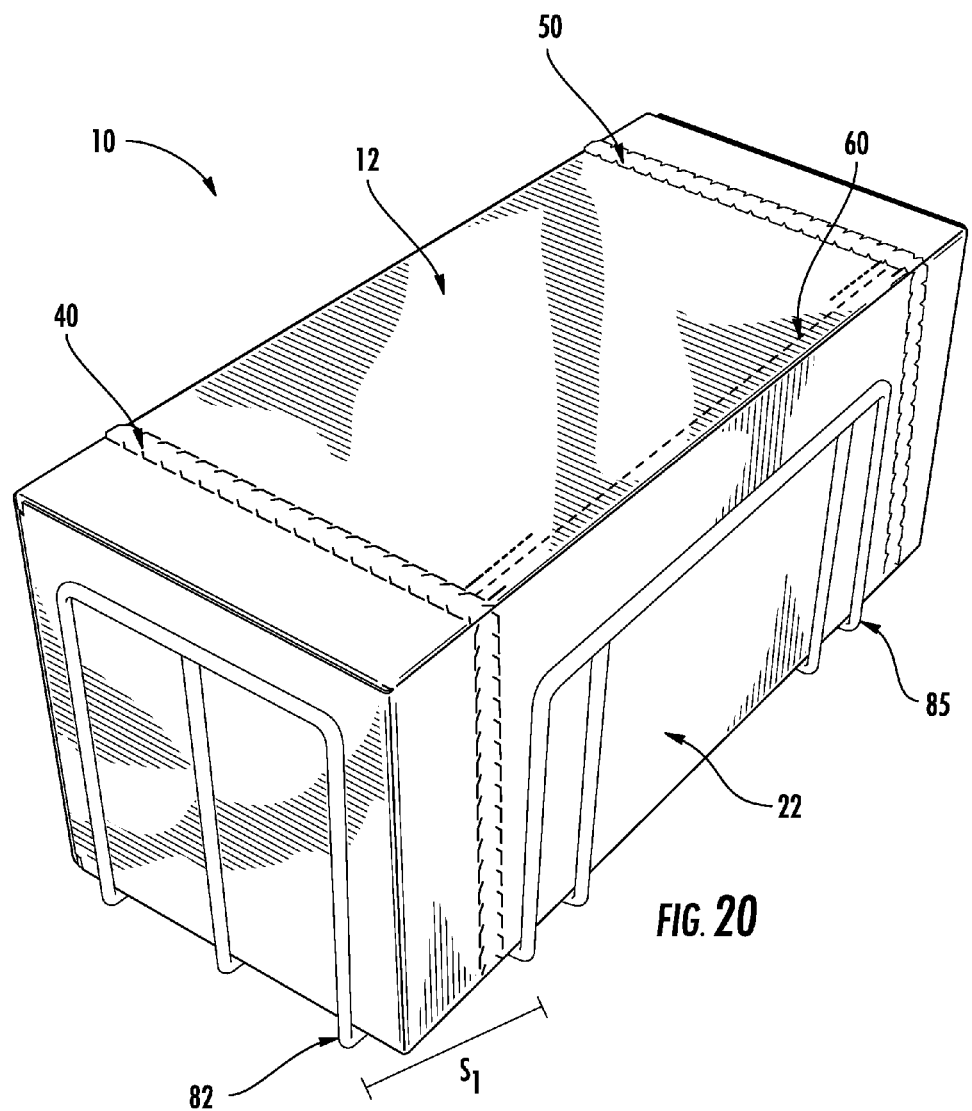
FIG. 20 is a perspective view of the basket shown in FIG. 19, wherein the carton shown in FIG. 1 is positioned within the basket, in accordance with example embodiments described herein.

With reference to FIG. 20, the basket may be configured to receive the carton 10, such as between the respective walls (e.g., front wall 85 and first wall 82). Additionally, in some embodiments, adjacent walls may be spaced apart to provide access to the removable features when the carton defines the closed configuration. For example, the front wall 85 of the basket 80 may be spaced apart ($S_1$) from the first wall 82 to provide access to the first removable feature 40 defined in the front surface 22 of the carton 10. Likewise, the front wall 85 of the basket 80 may be spaced apart from the second wall 84 to provide access to the second removable feature 50 defined in the front surface 22 of the carton 10.

Figure 21:
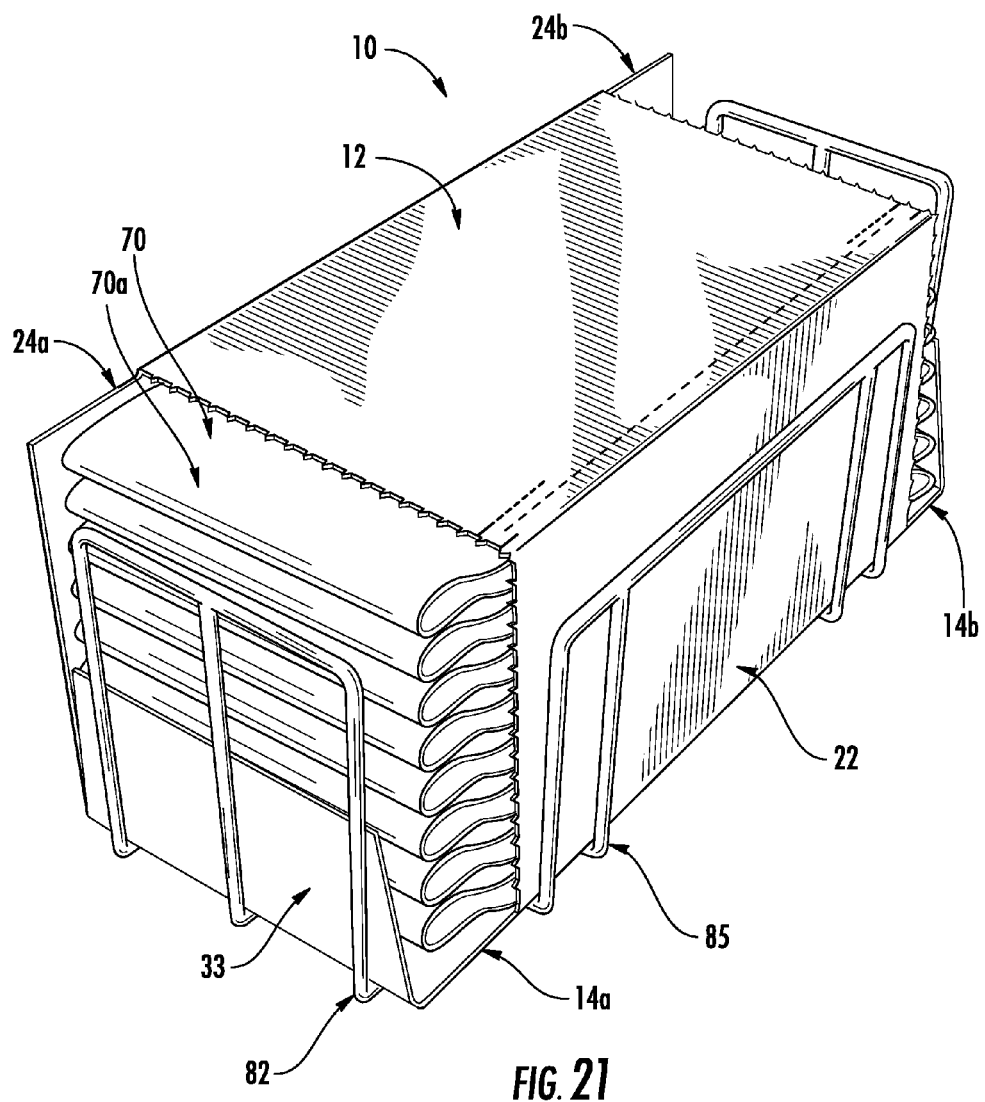
FIG. 21 is a perspective view of the basket and carton shown in FIG. 20, wherein a portion of the right end of the carton and a portion of the left end of the carton have each been removed to form a dispensing configuration for the product stored therein, in accordance with example embodiments described herein.

Additionally, in some embodiments, adjacent walls may be spaced apart to provide access to the product when the carton defines a dispensing configuration. For example, with reference to FIG. 21, the front wall 85 of the basket 80 may be spaced apart from the first wall 82 to provide access to the first portion 70a of each of the plurality of product 70. Likewise, the front wall 85 of the basket 80 may be spaced apart from the second wall 84 to provide access to the second portion 70b of each of the plurality of product 70.

Figure 22:
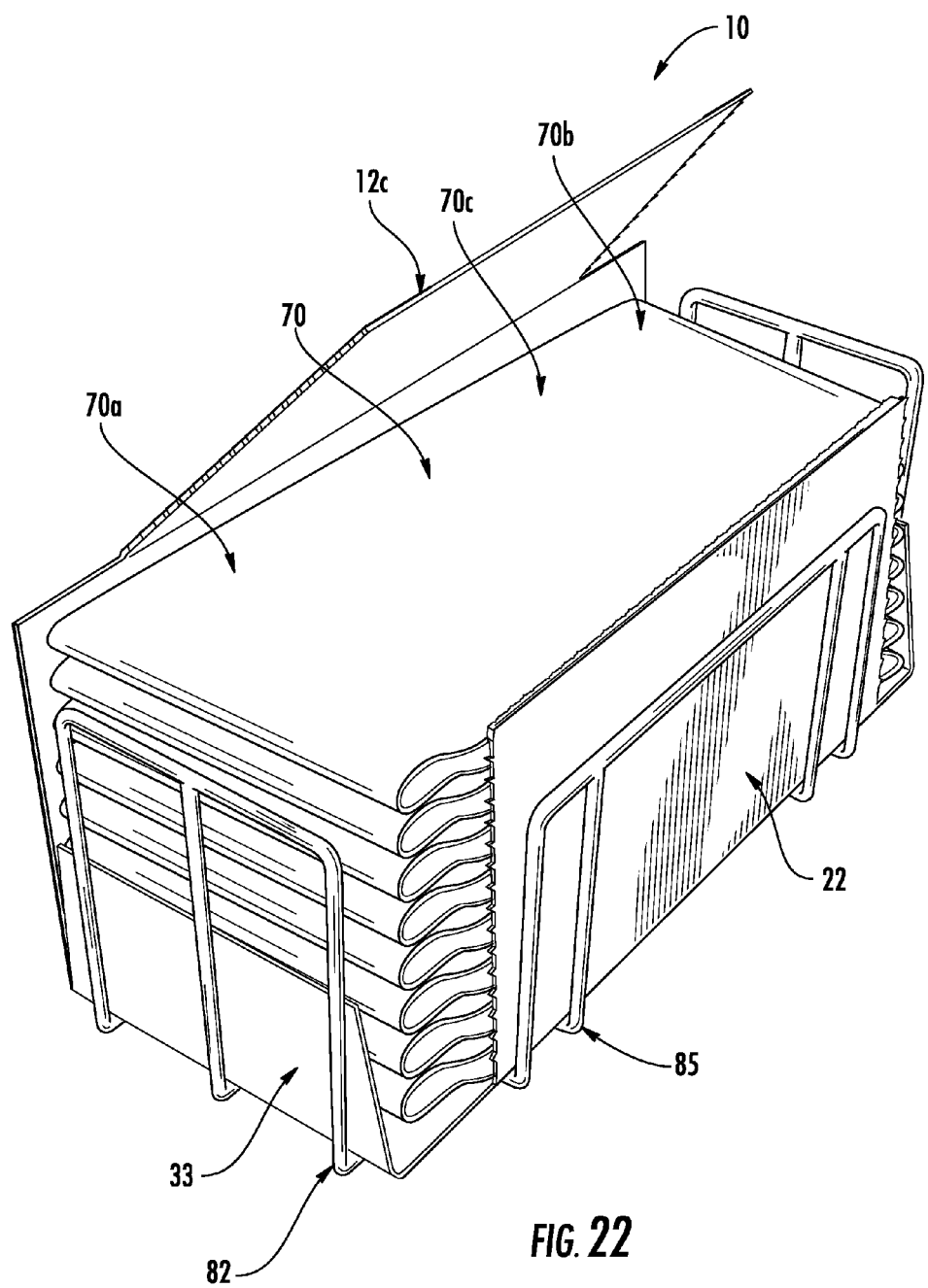
FIG. 22 is a perspective view of the basket and carton shown in FIG. 20, wherein a portion of the right end of the carton, a portion of the left end of the carton, and a portion of the top surface have each been removed to form a dispensing configuration for the product stored therein, in accordance with example embodiments described herein.

Along these same lines, in some embodiments, with reference to FIG. 20, the basket 80 may be configured to provide access to the third removable feature 60 when the carton 10 is in the closed configuration. For example, the basket 80 may not define a top surface so as to provide access to the top surface 12 of the carton 10 when the carton 10 is received by the basket 80. Further, with reference to FIG. 22, the basket 80 may be configured to provide access to the third portion 70c of each of the plurality of product 70 when the carton 10 is in a dispensing configuration.

Additionally, as noted above with respect to the designed tabs, it may be beneficial to promote dispensing of only one product at a time. Thus, in some embodiments, the first wall 82 and/or second wall 84 of the basket 80 may be defined to extend upwardly to promote removal of each product in a vertical manner and then a horizontal manner. Such a process may encourage removal of only one product at a time by facilitating the disengagement of the product to be dispensed from other products.

Figure 23:
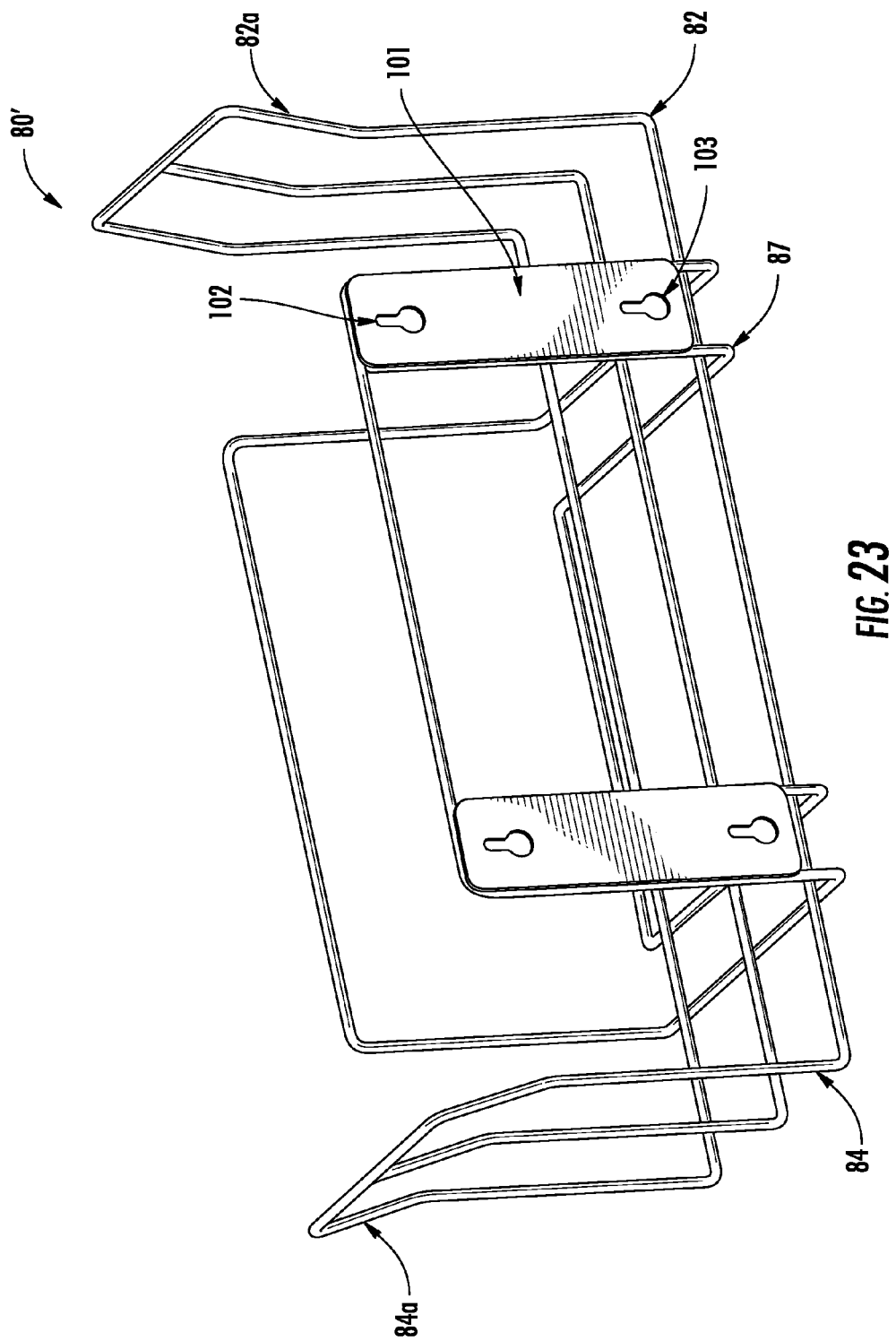
FIG. 23 is a perspective view of another basket for holding the carton shown in FIG. 1, in accordance with example embodiments described herein.

Additionally, in some embodiments, the basket may be configured to be mounted to a wall. For example, the basket may further comprise a mounting structure configured to be mounted to the wall. For example, with reference to FIG. 23, another example basket 80' comprises two mounting structures 101 attached to wires of the back wall 87. Each mounting structure 101 defines a first aperture 102 and a second aperture 103 for receiving mounting fasteners (e.g., screws) for mounting to a wall (not shown).

Additionally, in some embodiments, the basket 80' may be configured to allow for easy dispensing of the products contained in the carton 10 (shown in FIG. 22) by defining at least one of the first wall 82 or second wall 84 to extend outwardly and upwardly. For example, with reference to FIG. 23, the first wall 82 of the basket 80' defines a portion 82a that extends outwardly and upwardly to allow for easy dispensing of the products contained in the carton 10 (shown in FIG. 22). Likewise, with reference to FIG. 23, the second wall 84 of the basket 80' defines a portion 84a that extends outwardly and upwardly to allow for easy dispensing of the products contained in the carton 10 (shown in FIG. 22).

Figure 24:
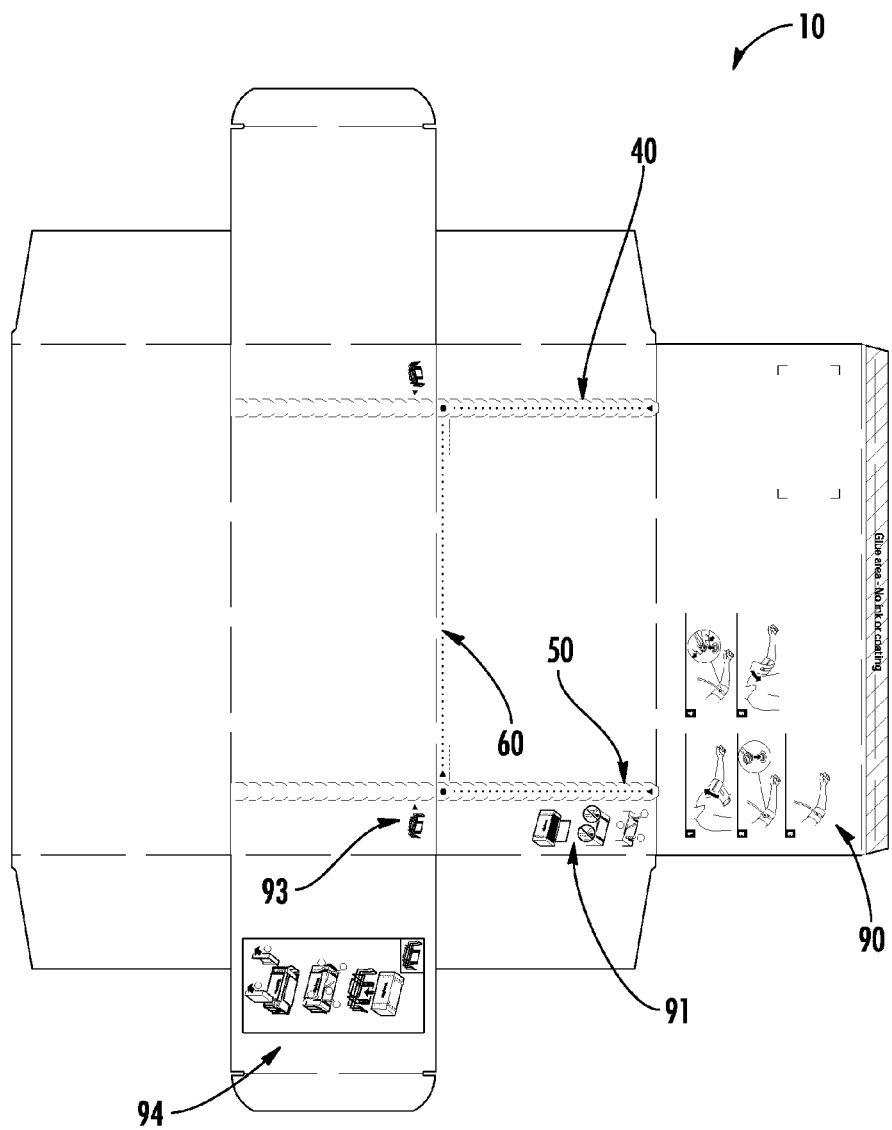
FIG. 24 is a top view of the carton shown in FIG. 1 disposed in an unfolded configuration, in accordance with example embodiments described herein.

In some embodiments, the carton 10 may define an unfolded configuration and may be configured to be folded into a closed configuration. For example, the carton 10 is illustrated in an unfolded configuration in FIG. 24. The carton 10 defines the first removable feature 40, the second removable feature 50, and the third removable feature 60 and the front surface, back surface, top surface, bottom surface, first end, and second end (not labeled). Additionally, the carton may define one or more illustrations that aid a user in forming a dispensing configuration. For example, illustration 91 provides instructions for removing the third portion of the top surface to form the third dispensing configuration. Illustration 94 provides instructions for positioning the carton inside a basket and removing a portion of the first end and a portion of the second end to form the fourth dispensing configuration. Along these same lines, the carton may comprise other illustrations, such as for providing information about positioning the carton within the basket properly (e.g., illustration 93) or proper use of one of the products, such as proper use of a disposable blood pressure cuff (e.g., illustration 90).

Another embodiment of the present invention is a method of manufacturing a carton for dispensing a plurality of products stored therein according to any example embodiments described herein. For example, the method may comprise providing a carton defining a top surface, a bottom surface, a first end, and a second end. The method may further comprise defining a first removable feature within the top surface proximate the first end. The first removable feature may be configured to be selectively removed from the top surface to enable removal of a portion of the first end. The method may further include defining a second removable feature within the top surface proximate the second end. The second removable feature may be configured to be selectively removed from the top surface to enable removal of a portion of the second end. The method may further include defining a third removable feature within the top surface. The third removable feature may be configured to be selectively removed from the top surface to enable removal of a portion of the top surface. The carton may define a closed configuration and a dispensing configuration. The dispensing configuration may be defined by at least one of the portion of the first end being removed, the portion of the second end being removed, and/or the portion of the top surface being removed.

In some embodiments, the carton may define a front surface and a back surface, and the method may further include defining the first removable feature by defining the first removable feature within a portion of the front surface proximate the first end. The method may further include defining the second removable feature by defining the second removable feature within a portion of the front surface proximate the second end.

In some embodiments, the method may further include defining the first removable feature by defining a perforation within the top surface. Additionally, the method may further include defining the second removable feature by defining a perforation within the top surface. Further, the method may include defining the third removable feature by defining a tear strip within the top surface.

Some embodiments of the present invention provide a number of advantages. For example, some embodiments of the carton described herein provide a user selectable dispensing configuration that is adaptable to the user's needs. Another advantage includes, in some embodiments, encouraging removal of only one product at a time to help prevent contamination. Moreover, the carton may be designed to be received by a basket for easy mounting and dispensing possibilities.

Many modifications and other embodiments of the inventions set forth herein will come to mind to one skilled in the art to which these embodiments pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A carton for dispensing a plurality of products stored therein, the carton defining a top surface, a bottom surface, a front surface, a back surface, a first end, and a second end, the carton comprising:
   a first removable feature associated with the top surface and the front surface and positioned proximate the first end of the carton, wherein the first removable feature is configured to be selectively removed from the top surface and the front surface to enable removal of a first portion of the first end, a first portion of the top surface, and a first portion of the front surface, wherein a first tab, a first portion of the bottom surface and a first portion of the back surface remains after removal of the first portion of the first end, the first portion of the top surface, and the first portion of the front surface;
   a second removable feature associated with the top surface and the front surface and positioned proximate the second end of the carton, wherein the second removable feature is configured to be selectively removed from the top surface and the front surface to enable removal of a first portion of the second end, a second portion of the top surface, and a second portion of the front surface, wherein a second tab, a second portion of the bottom surface, and a second portion of the back surface remains after removal of the first portion of the second end, the second portion of the top surface, and the second portion of the front surface;
   a third removable feature associated with the top surface and positioned between the first removable feature and the second removable feature, wherein the third removable feature is configured to be selectively removed from the top surface to enable removal of a third portion of the top surface, wherein at least a portion of the first removable feature and at least a portion of the second removable feature are each positioned adjacently to the third removable feature; and
   wherein the carton defines a closed configuration and a dispensing configuration, wherein the dispensing configuration is defined by at least one of:
      the first portion of the first end, the first portion of the top surface, and the first portion of the front surface being removed;
      the first portion of the second end, the second portion of the top surface, and the second portion of the front surface being removed; or
      the third portion of the top surface being removed,
   wherein, when in the dispensing configuration, the entire back surface and bottom surface of the carton remain to define a support for the plurality of products when the carton is in the dispensing configuration.

2. The carton according to claim 1, wherein the dispensing configuration is defined by the first portion of the first end being removed to reveal a first portion of each product for dispensing.

3. The carton according to claim 2, wherein the first tab extends upwardly from the first portion of the bottom surface, wherein the tab is configured to encourage the product to be removed generally vertically before being removed generally horizontally from the carton when the carton is in the dispensing configuration.

4. The carton according to claim 1, wherein the dispensing configuration is defined by the third portion of the top surface being removed to reveal a third portion of each product for dispensing.

5. The carton according to claim 1, wherein the dispensing configuration is defined by the first portion of the first end being removed to reveal a first portion of each product for dispensing and the first portion of the second end being removed to reveal a second portion of each product for dispensing.

6. The carton according to claim 1, wherein the dispensing configuration is defined by the first portion of the first end being removed to reveal a first portion of each product for dispensing, the first portion of the second end being removed to reveal a second portion of each product for dispensing, and the third portion of the top surface being removed to reveal a third portion of each product for dispensing.

7. The carton according to claim 1, wherein the first removable feature is defined within the top surface and the front surface to extend along a first plane, wherein the second removable feature is defined within the top surface and the front surface to extend along a second plane, wherein the third removable feature is defined within the top surface to extend along a third plane, and wherein the first plane and the second plane are each perpendicular to the third plane.

8. The carton according to claim 1, wherein, in the closed configuration, the carton defines an enclosed volume configured to store the plurality of products therein for shipment purposes.

9. The carton according to claim 1, wherein the first removable feature and the second removable feature each comprises a perforation; and wherein the third removable feature comprises a tear strip.

10. A system comprising:
    a plurality of products; and
    a carton for dispensing and storing the plurality of products, the carton defining a top surface, a bottom surface, a front surface, a back surface, a first end, and a second end, the carton comprising:
       a first removable feature associated with the top surface and the front surface and positioned proximate the first end of the carton, wherein the first removable feature is configured to be selectively removed from the top surface and the front surface to enable removal of a first portion of the first end, a first portion of the top surface, and a first portion of the front surface, wherein a first tab, a first portion of the bottom surface, and a first portion of the back surface remains after removal of the first portion of the first end, the first portion of the top surface, and the first portion of the front surface;
       a second removable feature associated with the top surface and the front surface and positioned proximate the second end of the carton, wherein the second removable feature is configured to be selectively removed from the top surface and the front surface to enable removal of a first portion of the second end, a second portion of the top surface, and a second portion of the front surface, wherein a second tab, a second portion of the back surface, and a second portion of the bottom surface remains after removal of the first portion of the second end, the second portion of the top surface, and the second portion of the front surface; and a third removable feature associated with the top surface and positioned between the first removable feature and the second removable feature, wherein the third removable feature is configured to be selectively removed from the top surface to enable removal of a third portion of the top surface, wherein at least a portion of the first removable feature and at least a portion of the second removable feature are each positioned adjacently to the third removable feature; and wherein the carton defines a closed configuration and a dispensing configuration, wherein the dispensing configuration is defined by at least one of:

the first portion of the first end, the first portion of the top surface, and the first portion of the front surface being removed;

the first portion of the second end, the second portion of the top surface, and the second portion of the front surface being removed; or the third portion of the top surface being removed, wherein, when in the dispensing configuration, the entire back surface and bottom surface of the carton remain to define a support for the plurality of products when the carton is in the dispensing configuration.

11. The system according to claim 10, wherein the dispensing configuration is defined by the first portion of the first end being removed to reveal a first portion of each product for dispensing.

12. A method for manufacturing a carton for dispensing a plurality of products stored therein, the method comprising:

providing the carton defining a top surface, a bottom surface, a front surface, a back surface, a first end, and a second end;

defining a first removable feature within the top surface and the front surface proximate the first end of the carton, wherein the first removable feature is configured to be selectively removed from the top surface and the front surface to enable removal of a first portion of the first end, a first portion of the top surface, and a first portion of the front surface, wherein a first tab, a first portion of the bottom surface, and a first portion of the back surface remains after removal of the first portion of the first end, the first portion of the top surface, and the first portion of the front surface;

defining a second removable feature within the top surface and the front surface proximate the second end of the carton, wherein the second removable feature is configured to be selectively removed from the top surface and the front surface to enable removal of a first portion of the second end, a second portion of the top surface, and a second portion of the front surface, wherein a second tab, a second portion of the bottom surface, and a second portion of the back surface remains after removal of the first portion of the second end, the second portion of the top surface, and the second portion of the front surface;

defining a third removable feature within the top surface extending between the first removable feature and the second removable feature, wherein the third removable feature is configured to be selectively removed from the top surface to enable removal of a third portion of the top surface, wherein at least a portion of the first removable feature and at least a portion of the second removable feature are each positioned adjacently to the third removable feature; and wherein the carton defines a closed configuration and a dispensing configuration, wherein the dispensing configuration is defined by at least one of:

the first portion of the first end, the first portion of the top surface, and the first portion of the front surface being removed;

the first portion of the second end, the second portion of the top surface, and the second portion of the front surface being removed; or the third portion of the top surface being removed, wherein, when in the dispensing configuration, the entire back surface and bottom surface of the carton remain to define a support for the plurality of products when the carton is in the dispensing configuration.

13. The method according to claim 12, wherein defining the first removable feature comprises defining a perforation within the top surface, wherein defining the second removable feature comprises defining a perforation within the top surface; and wherein defining the third removable feature comprises defining a tear strip within the top surface.

* * * * *